US007807670B2

(12) United States Patent
Yoakim et al.

(10) Patent No.: US 7,807,670 B2
(45) Date of Patent: Oct. 5, 2010

(54) INHIBITORS OF PAPILLOMA VIRUS

(75) Inventors: Christiane Yoakim, Laval (CA); Bruno Hache, Prevost (CA); William W. Ogilvie, Ottawa (CA); Jeffrey O'Meara, Boisbriand (CA); Peter White, Montreal (CA); Nathalie Goudreau, Mont-Royal (CA)

(73) Assignee: Boehringer Ingelheim Canada Ltd., Laval, Quebec (CA)

( * ) Notice: Subject to any disclaimer, the term of this patent is extended or adjusted under 35 U.S.C. 154(b) by 97 days.

(21) Appl. No.: 12/270,207

(22) Filed: Nov. 13, 2008

(65) Prior Publication Data
US 2010/0041649 A1 Feb. 18, 2010

Related U.S. Application Data

(62) Division of application No. 11/382,969, filed on May 12, 2006, now Pat. No. 7,528,167, which is a division of application No. 10/772,721, filed on Feb. 4, 2004, now Pat. No. 7,119,099, which is a division of application No. 10/023,975, filed on Dec. 17, 2001, now Pat. No. 6,759,409.

(60) Provisional application No. 60/256,706, filed on Dec. 18, 2000.

(51) Int. Cl.
*A61K 31/343* (2006.01)
*A61K 31/5377* (2006.01)
*A61P 31/12* (2006.01)
*C07D 307/94* (2006.01)
*C07D 265/30* (2006.01)

(52) U.S. Cl. ............... 514/231.5; 514/462; 544/70; 549/435

(58) Field of Classification Search .................. None
See application file for complete search history.

(56) References Cited

U.S. PATENT DOCUMENTS 6,759,409 B2* 7/2004 Yoakim et al. ........... 514/231.5

FOREIGN PATENT DOCUMENTS

WO WO 00/17206 A1 3/2000
WO WO 00/18772 A1 4/2000

OTHER PUBLICATIONS

English Translation of Office Action for Japanese Patent Application No. 2002-551975.
Shah, et al; "Papillomaviruses", Fields Virology, 3d ed, Ch. 66, 2077-2109, 1996.
English-language translation of "Chemistry of Heterocyclic Compounds", vol. 23, #11 (1987), M. Yu Krysin, et al.
Beutner, et al; "Therapeutic Approaches to Genital Warts"; Am. J. Med., 1997, 102(5A), 28-37.

Hughes, et al; "E1 Protein of Human Papollomavirus is a DNA Helicase/ATP Pase"; Nucleic Acids Res., 1993,vol. 21, No. 25, 5817-5823.
Kuo, et al; "Cell-free Replication of the Human Papillomavirus DNA with Homologous Viral E1 and E2 Proteins and Human Cell Extracts", J. Biol. Chem., 1994, vol. 269, No. 39, 24058-24065.
Seo, et al; "Bovine papilloma virus (BPV)-encoded E1 protein contains multiple activities required for BPV DNA replication"; Proc. natl. Acad. Sci USA; 1993: vol. 90. 702-706.
Yang, et al.; "The E1 protein of bovine papilloma virus 1 is an ATP-dependent DNA helicase"; Proc. Natl. Acad. Sci. USA; 1993; vol. 90, 5086-509.
MacPherson, et al; "The Bovine Papilloma Virus E1 Protein Has ATPase Activity Essential to Viral DNA Replication and Efficient Transformation in Cells"; Virology, 1994, 204, 403-408.
Mohr, et al; "Targeting the E1 Replication Protein to the Papillomavirus Origin of Replication by Complex Formation with the E2 Transactivator"; Science, 1990, 250; 1694-1699.
Seo, et al; "Bovine papilloma virus (BPV)-encoded E2 protein enhances binding of E1 protein to the BPV replication origin"; Proc. Natl. Acad. Sci. USA, 1993; vol. 90, 2865-2869.
Liu, et al; The Functions of Human Papillomavirus Type 11 E1, E2, and E2C Proteins in Cell-free DNA Replication; J. Biol. Chem., 1995, 270(45), 27283-27291.
Buckle, et al; "Antiallergic Activity of 2-Nitroindan-1,3-diones"; J. Med. Chem., 1973, vol. 16, No. 12, 1334-1339.
Koskinen, et al; "Diazo Transfer Reactions under Mildly Basic Conditions"; J. Chem. Soc. Chem. Commun.; 1990, 652-653.
Villeneuve, et al; "A Rapid, Mild and Acid-Free Procedure for the Preparation of Acyl Chlorides Including Formyl Chloride"; Tetrahedron Letters, 1997, vol. 38, No. 37, 6489-6492.

(Continued)

*Primary Examiner*—Kamal A Saeed
(74) *Attorney, Agent, or Firm*—Michael P. Morris; Mary-Ellen M. Devlin; Philip I. Datlow

(57) ABSTRACT

A compound of formula (I) or its enantiomers or diastereoisomers thereof:

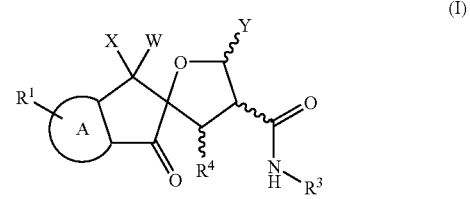

(I)

wherein: A,; X, W, R$^1$, Y; R$^3$; and R$^4$ are as defined herein.

The compounds of the invention may be used as inhibitors of the papilloma virus E1-E2-DNA complex. The invention further provides a method of treating or preventing human papilloma virus infection.

28 Claims, No Drawings

OTHER PUBLICATIONS

Krysin, et al; "1,3-Dipolar Cycloaddition of 2-Benzylideneindan-,3-Dionealpha-Oxide to Olefins"; Khimiya Geterotsiklicheskikh Soedinenii, 1987, 11, 1463-1466.

Reddy, et al; "Lewis Acid and Hexamethyldisilazane-Promoted Efficient Synthesis of N-Alkyl- and N-Arylimide Derivatives"; J. Org. Chem. 1997, 62, 2652-2654.

Chiang, et al; "Viral E1 and E2 proteins support replication of homologous and heterologous papillomaviral origins"; Proc. Natl. Acad. Sci. USA, 1992, vol. 89, 5799-5803.

McKay; "Binding of a Simian Viros 40 T Antigen-related Protein to DNA"; J. Mol. Biol. 1981, 145, 471-488.

* cited by examiner

INHIBITORS OF PAPILLOMA VIRUS

RELATED APPLICATIONS

This application is a divisional of U.S. Ser. No. 11/382,969, filed on May 12, 2006; Ser. No. 11/382,969, is a divisional of U.S. Ser. No. 10/772,721, filed on Feb. 4, 2004, now U.S. Pat. No. 7,119,099; Ser. No. 10/772,721, is a divisional of U.S. Ser. No. 10/023,975, filed on Dec. 17, 2001, now U.S. Pat. No. 6,759,409. This application claims the benefit of U.S. Provisional Application No. 60/256,706, filed on Dec. 18, 2000.

FIELD OF THE INVENTION

The present invention relates to compounds, compositions and methods for the treatment of papilloma virus (PV) infection, particularly human papilloma virus (HPV). In particular, the present invention provides novel indane derivatives, pharmaceutical compositions containing such derivatives and methods for using these compounds in the treatment of papilloma virus infection. More particularly, the present invention provides compounds, compositions and methods for inhibiting papilloma virus DNA replication by interfering with the E1-E2-DNA complex during initiation of DNA replication.

BACKGROUND OF THE INVENTION

Papillomaviruses are non-enveloped DNA viruses that induce hyperproliferative lesions of the epithelia. The papillomaviruses are widespread in nature and have been identified in higher vertebrates. Viruses have been characterized, amongst others, from humans, cattle, rabbits, horses, and dogs. The first papillomavirus was described in 1933 as cottontail rabbit papillomavirus (CRPV). Since then, the cottontail rabbit as well as bovine papillomavirus type 1 (BPV-1) have served as experimental prototypes for studies on papillomaviruses. Most animal papillomaviruses are associated with purely epithelial proliferative lesions, and most lesions in animals are cutaneous. In the human there are more than 75 types of papillomavirus that have been identified and they have been catalogued by site of infection: cutaneous epithelium and mucosal epithelium (oral and genital mucosa). The cutaneous-related diseases include flat warts, plantar warts, etc. The mucosal-related diseases include laryngeal papillomas and anogenital diseases comprising cervical carcinomas (Fields, 1996, Virology, 3rd ed. Lippincott—Raven Pub., Philadelphia, N.Y.).

There are more than 25 HPV types that are implicated in anogenital diseases, these are grouped into "low risk" and "high risk" types. The low risk types include HPV type 6, type 11 and type 13 and induce mostly benign lesions such as condyloma acuminata (genital warts) and low grade squamous intraepithelial lesions (SIL). In the United States there are 5 million people with genital warts of which 90% is attributed to HPV-6 and HPV-11. About 90% of SIL is also caused by low risk types 6 and 11. The other 10% of SIL is caused by high risk HPVs.

The high risk types are associated with high grade SIL and cervical cancer and include most frequently HPV types 16, 18, 31, 33, 35, 45, 52, and 58. The progression from low-grade SIL to high-grade SIL is much more frequent for lesions that contain high risk HPV-16 and 18 as compared to those that contain low risk HPV types. In addition, only four HPV types are detected frequently in cervical cancer (types 16, 18, 31 and 45). About 500,000 new cases of invasive cancer of the cervix are diagnosed annually worldwide (Fields, 1996, supra).

Treatments for genital warts include physical removal such as cryotherapy, $CO_2$ laser, electrosurgery, or surgical excision. Cytotoxic agents may also be used such as trichloroacetic acid (TCA), podophyllin or podofilox. Immunotherapy is also available such as Interferon or Imiquimod. These treatments are not completely effective in eliminating all viral particles and there is either a high cost incurred or uncomfortable side effects related thereto. In fact, there are currently no effective antiviral treatments for HPV infection since recurrent warts are common with all current therapies (Beutner & Ferenczy, 1997, Amer. J. Med., 102(5A), 28-37).

The ineffectiveness of the current methods to treat HPV infections has demonstrated the need to identify new means to control or eliminate such infections. In recent years, efforts have been directed towards finding antiviral compounds, and especially compounds capable of interfering with viral replication at the onset of infection (Hughes, 1993, Nucleic Acids Res. 21:5817-5823).

The life cycle of PV is closely coupled to keratinocyte differentiation. Infection is believed to occur at a site of tissue disruption in the basal epithelium. Unlike normal cells, the cellular DNA replication machinery is maintained as the cell undergoes vertical differentiation. As the infected cells undergo progressive differentiation the viral genome copy number and viral gene expression in turn increase, with the eventual late gene expression and virion assembly in terminally differentiated keratinocytes and the release of viral particles (Fields, supra).

The coding strands for each of the papillomavirus contain approximately ten designated translational open reading frames (ORFs) that have been classified as either early ORFs or late ORFs based on their location in the genome. E1 to E8 are expressed early in the viral replication cycle, and two late genes (L1 and L2) encode the major and minor capside proteins respectively. The E1 and E2 gene products function in viral DNA replication, whereas E5, E6 and E7 are expressed in connection with host cell proliferation. The L1 and L2 gene products are involved in virion structure. The function of the E3, E4 and E8 gene products is uncertain at present.

Studies of HPV have shown that proteins E1 and E2 are both essential and sufficient for viral DNA replication in vitro (Kuo et al., 1994, J. Biol. Chem. 30: 24058-24065). This requirement is similar to that of bovine papillomavirus type 1 (BPV-1). Indeed, there is a high degree of similarity between E1 and E2 proteins and the ori-sequences of all papillomaviruses (PV) regardless of the viral species and type (Kuo et al., 1994, supra).

Evidence emanating from studies of BPV-1 have shown that E1 possesses ATPase and helicase activities that are required in the initiation of viral DNA replication (Seo et al. 1993a, Proc. Natl. Acad. Sci. USA 90:702-706; Yang et al., 1993, Proc. Natl. Acad. Sci. 90:5086-5090; and MacPherson et al., 1994, 204:403-408).

The E2 protein is a transcriptional activator that binds to E1 protein and forms a complex that binds specifically to the ori sequence (Mohr et al., 1990, Science 250:1694-1699). It is believed that E2 enhances binding of E1 to the BPV origin of replication (See et al., 1993b, Proc. Natl. Acad. Sci., 90:2865-2869). In HPV, Lui et al. suggested that E2 stabilizes E1 binding to the ori (1995, J. Biol. Chem., 270(45):27283-27291).

To thwart this disease, a chemical entity that would interfere with viral DNA replication is therefore desirable. The present invention therefore provides such compounds, compositions or methods that inhibit papilloma viral replication. More particularly, the compounds and composition of the present invention interfere with the E1-E2-DNA complex during the viral replication cycle.

The present description refers to a number of documents, the content of which is herein incorporated by reference.

SUMMARY OF THE INVENTION

In a first aspect, the invention provides a compound of formula (I), or its enantiomers or diastereoisomers thereof:

(I)

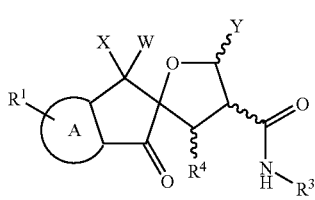

(form 1)

wherein:

A is a 5- or 6-membered homocyclic ring, or a 5- or 6-membered heterocyclic ring containing 1 or more heteroatoms selected from N, O and S;

X is H and W is OH; or X and W together form a carbonyl group or an epoxide;

$R^1$ is H; or one or two substituents independently selected from the group consisting of: hydroxy; halo; lower alkyl; lower alkoxy; lower thioalkyl; haloalkyl (e.g. trifluoromethyl); or —C(O)$R^2$ wherein $R^2$ is lower alkyl, aryloxy or benzyloxy;

Y is phenyl optionally mono- or di-substituted with $R^5$ or C(O)$R^6$, wherein $R^5$ is lower alkyl, lower cycloalkyl, lower alkoxy, halo, hydroxy, nitrile or trifluoromethyl, and $R^6$ is lower alkyl, lower cycloalkyl, lower alkoxy, hydroxy or trifluoromethyl; said phenyl ring being optionally fused with a saturated or unsaturated 4 to 6-membered ring optionally containing a heteroatom selected from N, O and S;

or Y is a heterocycle (Het) containing one or more heteroatom selected from N, O or S, said Het optionally mono- or di-substituted with $R^5$ or C(O)$R^6$, wherein $R^5$ and $R^6$ are as defined above; said Het being optionally fused with a saturated or unsaturated 4 to 6-membered ring optionally containing a heteroatom selected from N, O and S;

or Y is ethylene-phenyl, said ethylene moiety being optionally mono-substituted with lower alkyl, wherein said phenyl ring is optionally mono- or di-substituted with $R^5$ or C(O)$R^6$, wherein $R^5$ and $R^6$ are as defined above; said phenyl ring being optionally fused with a saturated or unsaturated 4- to 6-membered ring optionally containing a heteroatom selected from N, O and S;

or Y is ethylene-Het, said ethylene moiety being optionally mono-substituted with lower alkyl, wherein Het is optionally mono- or di-substituted with $R^5$ or C(O)$R^6$, wherein $R^5$ and $R^6$ are as defined above; said Het being optionally fused with a saturated or unsaturated 4 to 6-membered ring optionally containing a heteroatom selected from N, O and S;

$R^3$ is selected from the group consisting of: lower alkyl, lower cycloalkyl, lower alkylene, aryl or lower aralkyl, all of which optionally mono- or di-substituted with:

lower alkyl, lower cycloalkyl, haloalkyl, halo, CN, azido, lower alkoxy, (lower alkyl)acyl, $C_{1-6}$ thioalkyl, $C_{1-6}$ alkylsulfonyl, NHC(O)-lower alkyl, NHC(O)-aryl, NHC(O)—O-lower alkyl, NHC(O)O-aryl, aryl, aryloxy, hydroxy, nitro, amino, or Het, said Hot optionally mono- or di-substituted with lower alkyl, lower cycloalkyl, lower alkoxy, halo, hydroxy, nitrile, trifluoromethyl, C(O)$R^6$ wherein $R^6$ is as defined above;

said lower cycloalkyl, aryl, lower aralkyl or Het being optionally fused with a saturated or unsaturated 4 to 6-membered ring optionally containing a heteroatom selected from N, O and S;

and $R^4$ is a carboxylic acid, a salt or an ester thereof;

and wherein wavy lines represent bonds of unspecified stereochemistry;

and with the provisos that:

(1) when A is benzene, $R^1$ is hydrogen, X and W together form a carbonyl group and Y is 4-methylphenyl, then $R^3$ cannot be benzyl, 3-fluorophenyl, or 4-nitrophenyl;

(2) when A is benzene, $R^1$ is hydrogen, X and W together form a carbonyl group and $R^3$ is cyclohexyl, then Y cannot be 4-iodophenyl or 4-methylphenyl;

(3) when A is benzene, $R^1$ is hydrogen, X and W together form a carbonyl group and Y is 4-fluorophenyl, then $R^3$ cannot be 4-ethyloxycarbonylphenyl;

(4) when A is benzene, $R^1$ is hydrogen, X and W together form a carbonyl group and Y is 2-methylphenyl then $R^3$ cannot be 4-nitrophenyl;

(5) when A is benzene, $R^1$ is hydrogen, X and W together form a carbonyl group and Y is 2-methylphenyl, then $R^3$ cannot be phenyl or 2-bromo-4-methylphenyl;

(6) when A is benzene, $R^1$ is hydrogen, X and W together form a carbonyl group and Y is 4-chlorophenyl, then $R^3$ cannot be 2-methoxyphenyl or 1,3-benzodioxolyl;

(7) when A is benzene, $R^1$ is hydrogen, X and W together form a carbonyl group and Y is 4-ethylphenyl, then $R^3$ cannot be 3-fluorophenyl; and (8) when A is benzene, $R^1$ is hydrogen, X and W together form a carbonyl group and Y is phenyl, then $R^3$ cannot be phenyl.

Alternatively, the first aspect of the invention provides compounds having the following formulae, selected from the group consisting of:

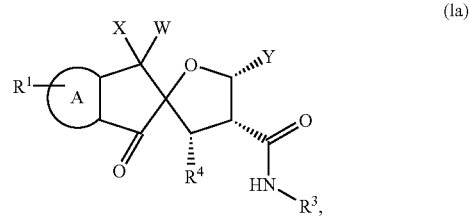

(Ia)

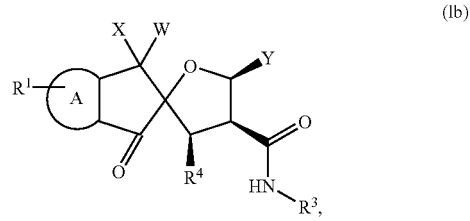

(Ib)

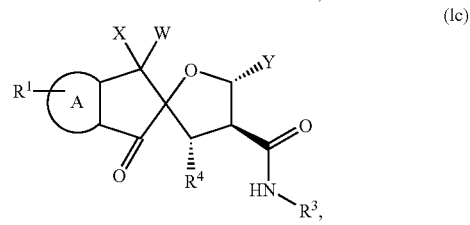

(Ic)

-continued

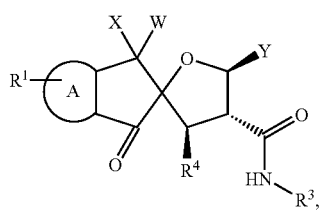
(Id)

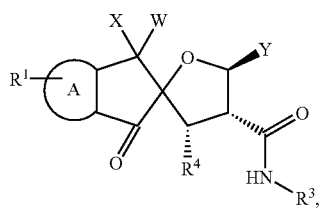
(Ie)

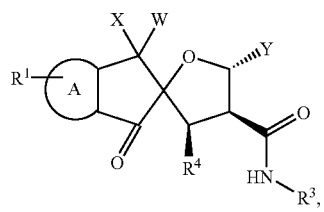
(If)

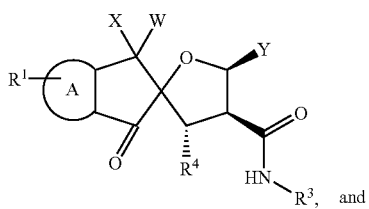
(Ig)

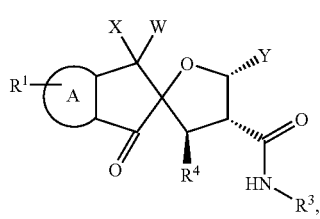
(Ih)

wherein A, X, W, $R^1$, Y, $R^3$ and $R^4$ are as defined above, with the provisos indicated above.

Compounds of the invention may also be represented by formula I in forms (2) and (3):

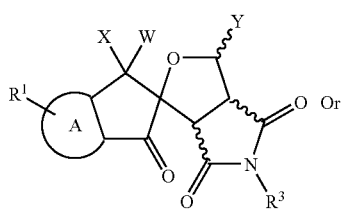
(form 2)

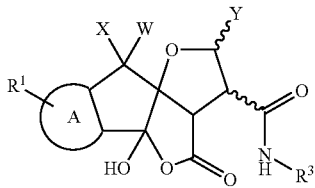
(form 3)

wherein A, X, W, $R^1$, Y and $R^3$ are as defined above, with the provisos indicated above.

As will be recognized by persons skilled in the art, the compounds in forms (2) and (3) are readily converted to compounds of formula (I) in form (1). Without wishing to be bound by theory, it is believed that the compounds of formula (I) are in equilibrium between forms (1), (2) or (3) depending on the solvent and the pH in which they are dissolved. It has however been demonstrated that compounds of formula (I) are biologically active in form (1), and that the compounds in forms (2) and (3) will hydrolyze in conditions reproducing mammalian plasma (pH 7.4), to yield biologically active form (1).

In a second aspect, the invention provides a pharmaceutical composition comprising an anti-papillomavirus virally effective amount of a compound of formula (I) or a therapeutically acceptable salt or ester thereof in admixture with a pharmaceutically acceptable carrier medium or auxiliary agent.

In a third aspect, the invention provides a method for treating a papillomavirus viral infection in a mammal by administering to the mammal an anti-papilloma virus virally effective amount of the compound of formula (I) or a therapeutically acceptable salt or ester thereof, or a composition as described above, (all without the provisos indicated above for formula (I).

In fourth aspect, the invention provides a method for inhibiting the replication of papillomavirus by exposing virally infected cells to an amount of the compounds of formula (I) inhibiting the papilloma virus E1-E2-DNA complex, or a therapeutically acceptable salt or ester thereof, or a composition as described above, (all without the provisos indicated above for formula (I).

In a fifth aspect the invention provides a use of compounds of formula (I) (without the provisos indicated above for formula (I)) for the manufacture of a medicament for treating a papillomavirus viral infection.

In an sixth aspect, the invention provides a method of preventing perinatal transmission of HPV from mother to baby, by administering a compound of formula (I) (without the provisos indicated above for formula (I)) to the mother prior to giving birth.

In a seventh aspect, the invention provides a use of compounds of formula (I) (without the provisos indicated above for formula (I)) for the manufacture of a medicament for preventing perinatal transmission of HPV from mother to baby prior to giving birth.

In an eighth aspect, the invention provides an intermediate compound of formula (vi):

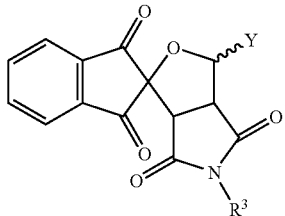

wherein Y and R³ are as defined above, or enantiomers or diastereoisomers thereof, with the provisos indicated above for formula (I).

In a ninth aspect, the invention provides an intermediate compound of formula (xx), said compound having trans/trans relative strereochemistry:

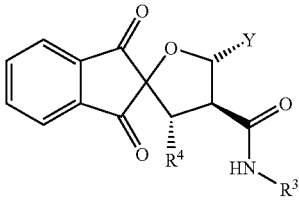

wherein Y, R³, and R⁴ are as defined above, with the provisos indicated above for formula (I).

In an tenth aspect, the invention provides an intermediate compound of formula (xxvi):

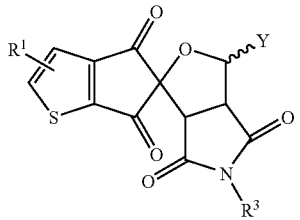

wherein R¹, R³ and Y are as defined above, or a salt or an ester thereof, or enantiomers and diastereoisomers thereof, without the provisos indicated above for formula (I).

In a eleventh aspect, the invention provides an intermediate compound of formula (xxxii):

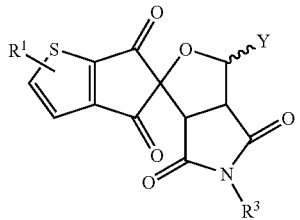

wherein R¹, R³ and Y are as defined above, or a salt or an ester thereof or enantiomers and diastereoisomers thereof, without the provisos indicated above for formula (I).

In a twelfth aspect, the invention provides a process for producing compounds of formula I',

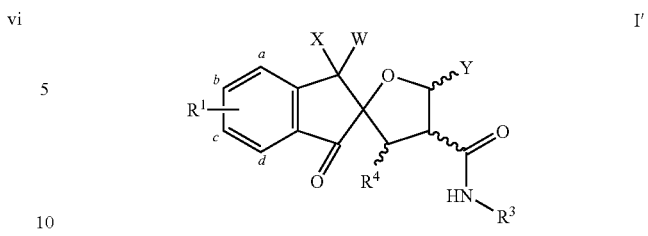

wherein X, R¹, W, Y, R³, and R⁴ are as defined above, with the provisos indicated above for formula (I), comprising:
a) hydrolyzing, in a mixture of aqueous base and a co-solvent, either intermediate compound vi or intermediate compound xx

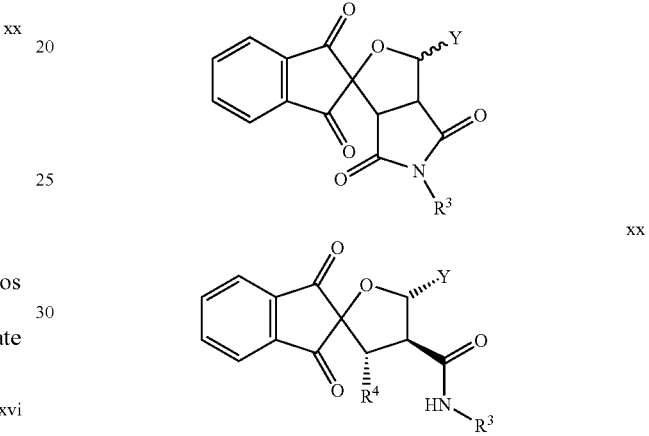

to produce compounds of formula I', wherein R³, R⁴, and Y are as defined above.

In a thirteenth aspect, the invention provides a process for producing compounds of formula I",

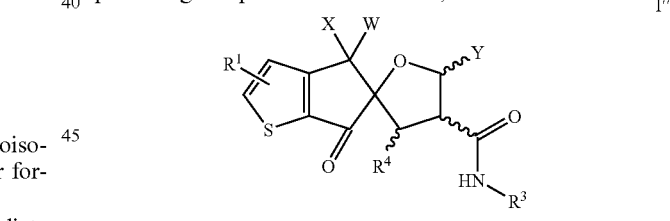

wherein X and W together form a carbonyl group, R⁴ is a carboxylic acid or an ester, and R¹, Y, and R³ are as defined above, without the provisos indicated above for formula (I), comprising:
a) hydrolyzing, in a mixture of aqueous base and a co-solvent, intermediate compound xxvi,

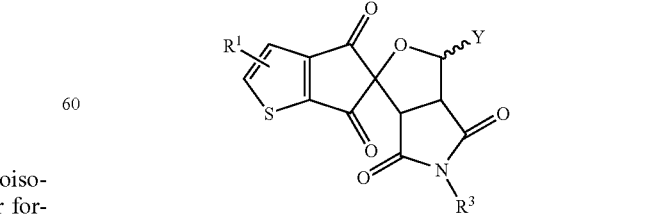

so as to produce compounds of formula I", wherein R¹, Y, and R³ are as defined above.

In a fourteenth aspect, the invention provides, a process for producing compounds of formula I''',

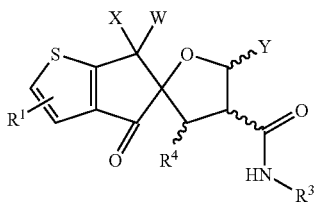

wherein X and W together form a carbonyl group, R⁴ is a carboxylic acid or an ester, and R¹, Y, and R³ are as defined above, without the provisos indicated above for formula (I), comprising:

a) hydrolyzing, in a mixture of aqueous base and a co-solvent, intermediate compound xxxii

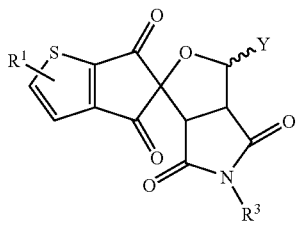

so as to produce compounds of formula I''', wherein R¹, Y, and R³ are as defined above.

DETAILED DESCRIPTION OF PREFERRED EMBODIMENTS

Definitions

As used herein, the following definitions apply unless otherwise noted:

The term "halo" as used herein means a halo radical selected from bromo, chloro, fluoro or iodo.

The term "lower alkyl" (or $C_{1-6}$ alkyl) as used herein, either alone or in combination with another radical, means straight or branched-chain alkyl radicals containing up to six carbon atoms and includes methyl, ethyl, propyl, butyl, hexyl, 1-methylethyl, 1-methylpropyl, 2-methylpropyl and 1,1-dimethylethyl. The term "$C_{0-6}$ alkyl" preceding a radical means that this radical can optionally be linked through a $C_{1-6}$ alkyl radical or the alkyl may be absent ($C_0$).

The term "lower cycloalkyl" as used herein, either alone or in combination with another radical, means saturated cyclic hydrocarbon radicals containing from three to seven carbon atoms and includes cyclopropyl, cyclobutyl, cyclopentyl, cyclohexyl and cycloheptyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "haloalkyl" as used herein means alkyl radical containing one to six carbon atoms wherein one or more hydrogen atom is replaced by a halogen atom (e.g. trifluoromethyl).

The term "amino" as used herein means an amino radical of formula —$NH_2$. The term "lower alkylamino" as used herein means alkylamino radicals containing one to six carbon atoms and includes methylamino, propylamino, (1-methylethyl)amino and (2-methylbutyl)amino. The term "di(lower alkyl)amino" means an amino radical having two lower alkyl substituents each of which contains one to six carbon atoms and includes dimethylamino, diethylamino, ethylmethylamino and the like.

The term "acyl" as used herein, either alone or in combination with another radical, refers to groups —C(O)R, wherein R is lower alkyl or lower alkoxy.

The term "$C_6$ or $C_{10}$ aryl" as used herein, either alone or in combination with another radical, means either an aromatic monocyclic system containing 6 carbon atoms or an aromatic cyclic system containing 10 carbon atoms. For example, aryl includes phenyl or naphthalene.

The term "$C_{7-16}$ aralkyl" as used herein, either alone or in combination with another radical, means an aryl as defined above linked through an alkyl group, wherein alkyl is as defined above containing from 1 to 6 carbon atoms. Aralkyl includes for example benzyl, and butylphenyl.

The term "Het" as used herein means a monovalent radical derived by removal of a hydrogen from a five- or six-membered, saturated or unsaturated heterocycle containing from one to three heteroatoms selected from nitrogen, oxygen and sulfur. Optionally, the heterocycle may bear one or two substituents; for example, N-oxido, lower alkyl, ($C_{1-3}$)alkyl-phenyl, lower alkoxy, halo, amino or lower alkylamino. Again optionally, the five- or six-membered heterocycle can be fused to a second cycloalkyl, an aryl (e.g. phenyl) or another heterocycle.

Examples of suitable heterocycles and optionally substituted heterocycles include morpholine, thiadiazole, quinoline, 3,4-methylene-dioxyphenyl, benzothiazole, pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)-thiazole, piperidine, 1-methylpiperidine, 1-methylpiperazine, 1,4-dioxane, pyridine, pyridine N-oxide, pyrimidine, 2,4-dihydroxypyrimidine, 2,4-dimethylpyrimidine, 2,6-dimethylpyridine, 1-methyl-1H-tetrazole, 2-methyl-2H-tetrazole, benzoxazole and thiazolo[4,5-b]-pyridine.

The term "pharmaceutically acceptable carrier" as used herein means a non-toxic, generally inert vehicle for the active ingredient which does not adversely affect the ingredient.

The term "effective amount" means a predetermined antiviral amount of the antiviral agent, i.e. an amount of the agent sufficient to be effective against the virus in vivo.

The compounds of formula (I) can be obtained in the form of therapeutically acceptable salts. The term "pharmaceutically acceptable salt" as used herein includes those derived from pharmaceutically acceptable bases. Examples of suitable bases include choline, ethanolamine and ethylenediamine. Na+, K+, and Ca++ salts are also contemplated to be within the scope of the invention (also see Pharmaceutical salts, Birge, S. M. et al., J. Pharm. Sci. (1977), 66, 1-19, incorporated herein by reference).

The term "pharmaceutically acceptable ester" as used herein, either alone or in combination with another radical, means esters of the compound of formula (I) in which the carboxyl function is replaced by an alkoxycarbonyl function:

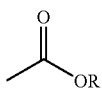

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters can be found in Design of prodrugs, Bundgaard, H. Ed. Elsevier (1985) incorporated herewith by reference. Such pharmaceutically acceptable esters are usually hydrolyzed in vivo when injected in a mammal and transformed into the acid form of the compound of formula (I).

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group.

In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

Preferred Embodiments

According to a first embodiment of this invention, preferably compounds of the invention are those in which ring A is a benzene ring, as represented by the formula I':

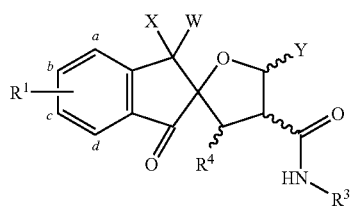

Wherein X, W, $R^1$, Y and $R^3$ are as defined above, with the provisos indicated above for formula (I). The compounds of formula I' exist in forms (1), (2) and (3), as described for the compounds of formula I.

Alternatively preferably, compounds of this invention are those in which ring A is a five-membered ring containing a sulfur atom, as represented by the formulae I" and I'":

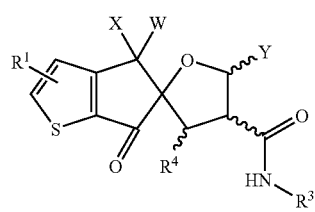

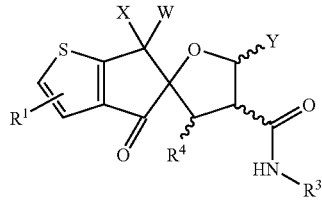

Wherein X, W, $R^1$, Y and $R^3$ are as defined above, without the provisos indicated above for formula (I)) The compounds of formulae I" and I'" exist in forms (1), (2) and (3), as described for the compounds of formula I.

Alternatively even more preferably, compounds of the e invention have the following formula:

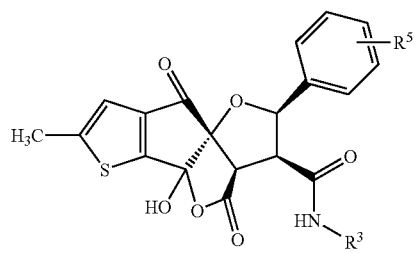

wherein $R^3$ and $R^5$ are as defined above without the provisos indicated above for formula (I).

The compounds of the present invention can be synthesized as racemic mixtures and then separated in their respective single diastereoisomers. All such diastereoisomers are contemplated within the scope of the present invention.

Preferably, such diastereoisomers include mixture of compounds with the following relative stereochemistry between [Y & C(O)NH—$R^3$] and [C(O)NH—$R^3$ & $R^4$]:

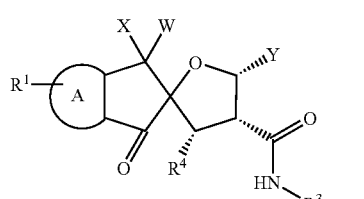

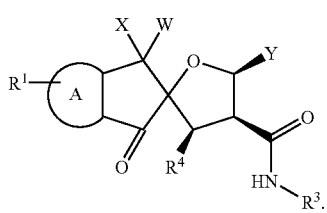

Formulas (Ia) and (Ib) both represent racemic mixtures of compounds with the relative stereochemistry referred to as "cis/cis".

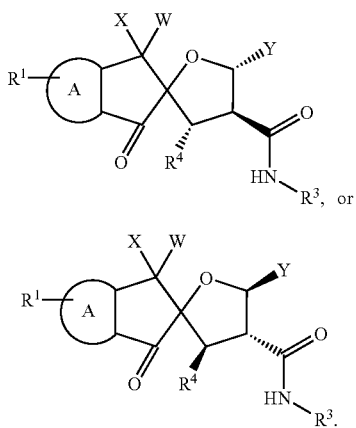
(Ic)

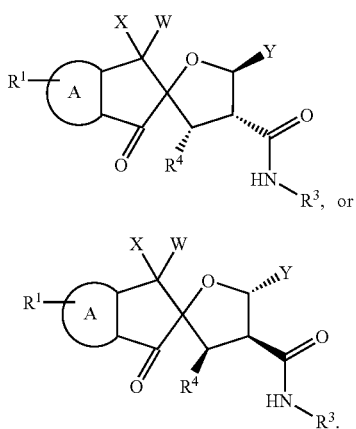 
(Id)

Formulas (Ic) and (Id) both represent racemic mixtures of compounds with the relative stereochemistry referred to as "trans/trans".

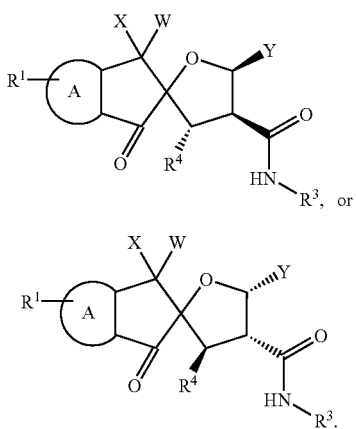
(Ie)

(If)

Formulas (Ie) and (If) both represent racemic mixtures of compounds with the relative stereochemistry referred to as "trans/cis".

(Ig)

(Ih)

Formula (Ig) and (Ih) both represent racemic mixtures of compounds with the relative stereochemistry referred to as "cis/trans".

More preferably, such diastereoisomers include mixture of compounds with the relative stereochemistry "cis/cis":

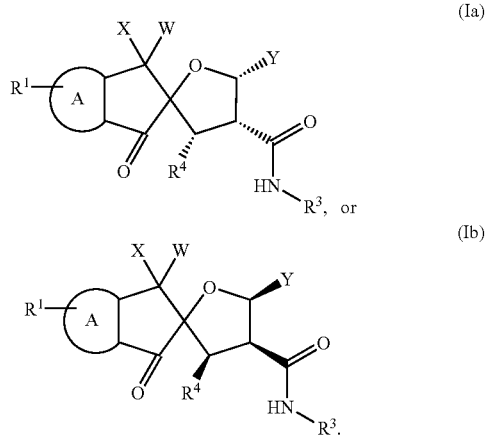
(Ia)

(Ib)

Also preferred are diastereoisomers with the relative stereochemistry "trans/trans":

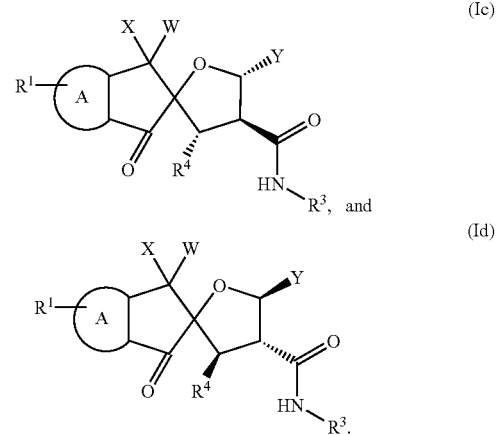
(Ic)

(Id)

Most preferably, compounds of formula (I), present in an "cis/cis" relative stereochemistry that can also be represented as follows:

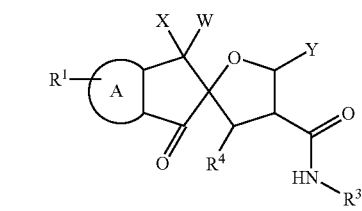

racemic mixture of Ia and Ib

Still most preferably, the invention comprises pure enantiomers of compounds of formula (Ia) or (Ib) with the relative stereochemistry "cis/cis":

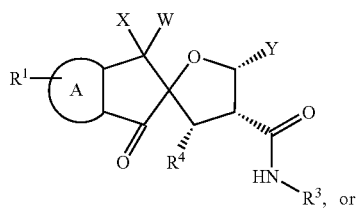
(Ia)

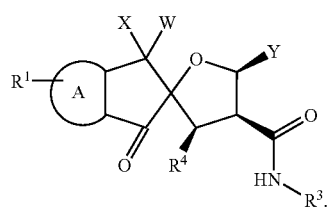
(Ib)

With respect to compounds of formulae I, I', I", I'", Ia, Ib, Ic, Id, Ie, If, Ig, and Ih, preferably X is H and W is OH; or X and W form a carbonyl group. Most preferably, X and W form a carbonyl group.

With respect to compounds of the formulae I', I" and I'" preferably A is phenyl or thiophene. Most preferably, A is thiophene.

With respect to compounds of the formulae I', I" and I'" preferably $R^1$ is H; or one or two substituents independently selected from the group consisting of: hydroxy; halo; lower alkyl; lower alkoxy; lower thioalkyl; haloalkyl (e.g. trifluoromethyl); or $C(O)R^2$ wherein $R^2$ is lower alkyl, aryloxy or benzyloxy.

More preferably, $R^1$ is H, halo or $C_{1-4}$ alkyl.

Even more preferably, $R^1$ is H, fluoro or methyl.

Most preferably, $R^1$ is H or methyl.

Preferably, Y is phenyl optionally mono- or di-substituted with $R^5$ or $C(O)R^6$, wherein $R^5$ is lower alkyl, lower cycloalkyl, lower alkoxy, halo, hydroxy, nitrile or trifluoromethyl, and $R^6$ is lower alkyl, lower cycloalkyl, lower alkoxy, hydroxy or trifluoromethyl; said phenyl ring being optionally fused with a saturated or unsaturated 4 to 6-membered ring optionally containing a heteroatom selected from N, O and S; or Y is ethylene-phenyl, said ethylene moiety being optionally mono-substituted with lower alkyl, wherein said phenyl ring is optionally mono- or di-substituted with $R^5$ or $C(O)R^6$, wherein $R^5$ and $R^6$ are as defined above; said phenyl ring being optionally fused with a saturated or unsaturated 4- to 6-membered ring optionally containing a heteroatom selected from N, O and S.

More preferably, Y is naphthyl, CH=CH-phenyl, $C(CH_3)$=CH-phenyl or phenyl, wherein the phenyl ring is optionally mono- or di-substituted at the 3, 4, or 5 position with $R^5$, wherein $R^5$ is halo, $C_{1-4}$ alkyl, hydroxy, $CF_3$ or NHC(O)-(lower alkyl).

Still more preferably, Y is phenyl optionally substituted with: 3,4-Cl; 3-F,4-Cl; 3-Cl,4-F; 3,4-Br; 3-F,4-CH$_3$; 3,4-CH$_3$; 3-CF$_3$, NHC(O)—(CH$_2$)$_3$CH$_3$ and

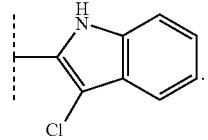

Most preferably, Y is phenyl optionally substituted with: 3,4-Cl and 3,4-Br.

Preferably, $R^3$ is selected from the group consisting of:

cyclohexyl; $C_{1-6}$ alkyl; $C_{1-6}$ thioalkyl; ($C_{1-6}$ alkyl)phenyl wherein the phenyl ring is optionally substituted with:
lower alkyl, CF$_3$, halo, CN, azido, lower alkoxy, (lower alkyl)acyl, $C_{1-6}$ thioalkyl, $C_{1-6}$ alkylsulfonyl, NHC(O)-lower alkyl, aryl, aryloxy, hydroxy, nitro, amino, or Het, said Het optionally mono- or di-substituted with lower alkyl, lower alkoxy, halo, hydroxy, nitrile, trifluoromethyl:

Even more preferably, $R^3$ is selected from the group consisting of:

$C_{1-6}$ alkyl; $C_{1-6}$ thioalkyl;

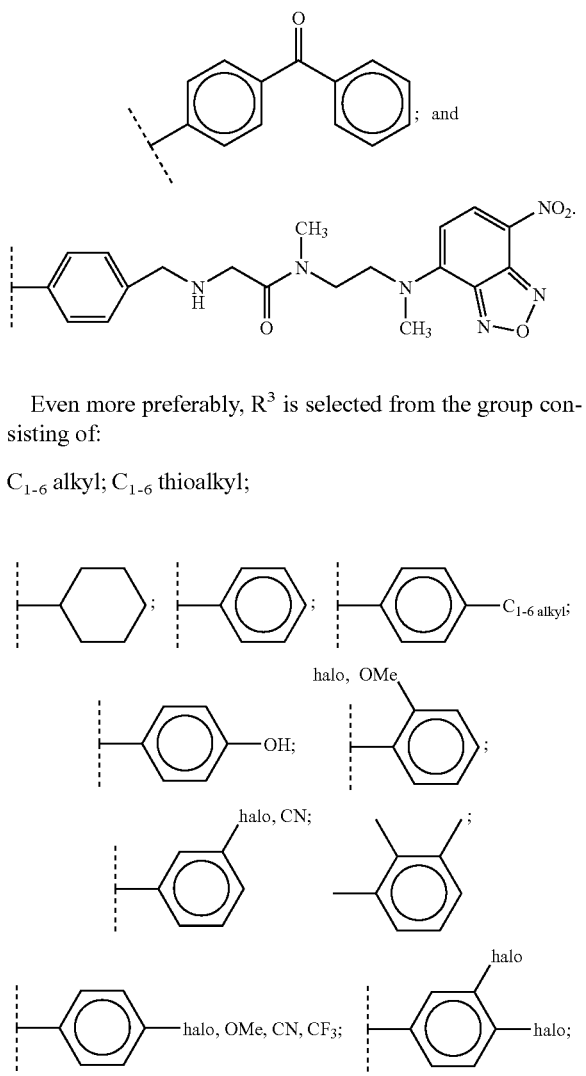

-continued
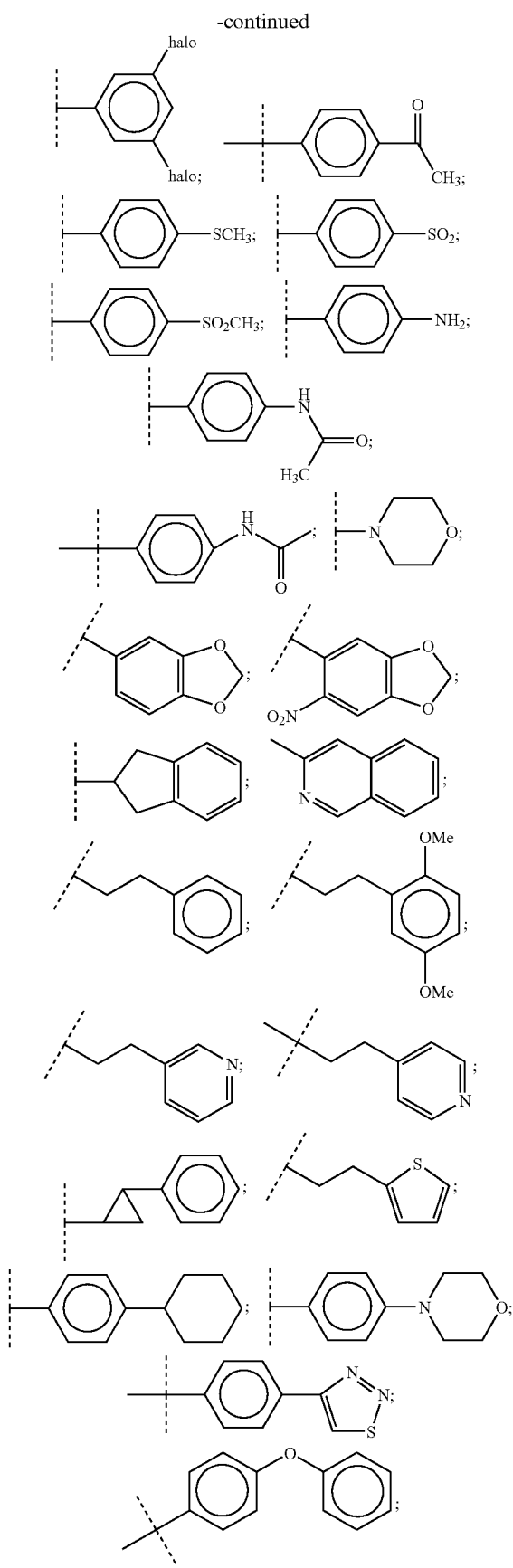
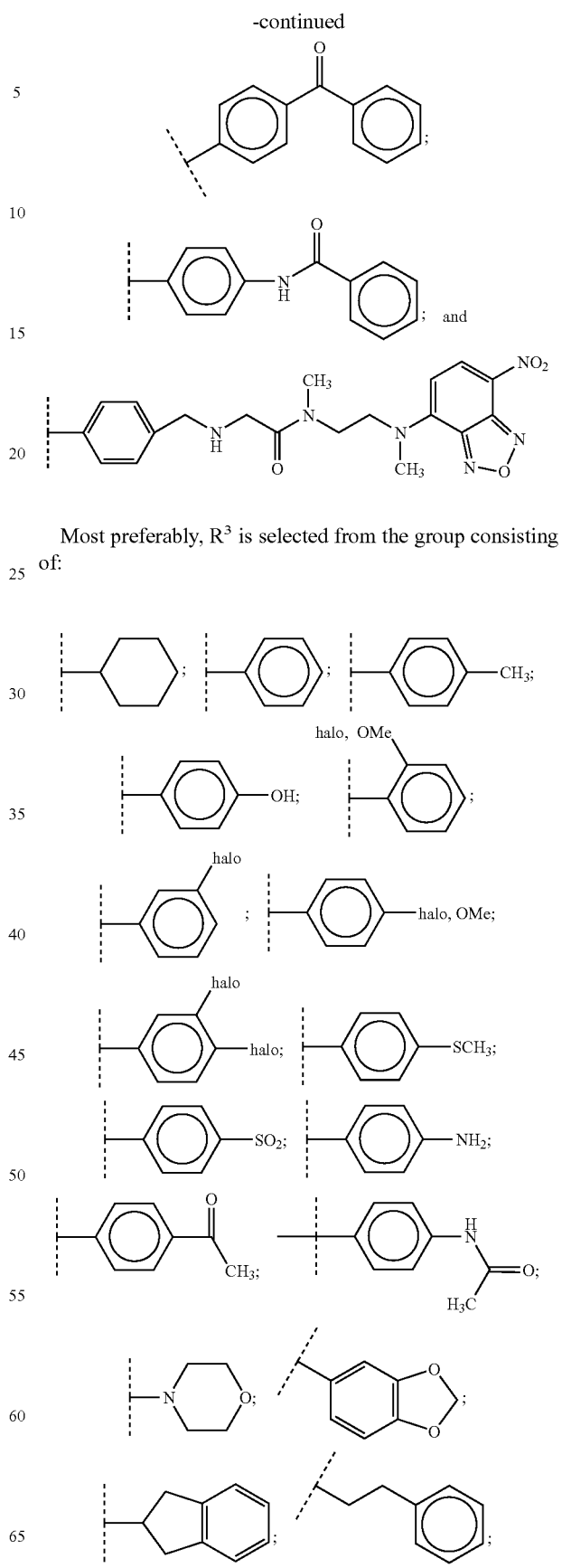
Most preferably, R³ is selected from the group consisting of:

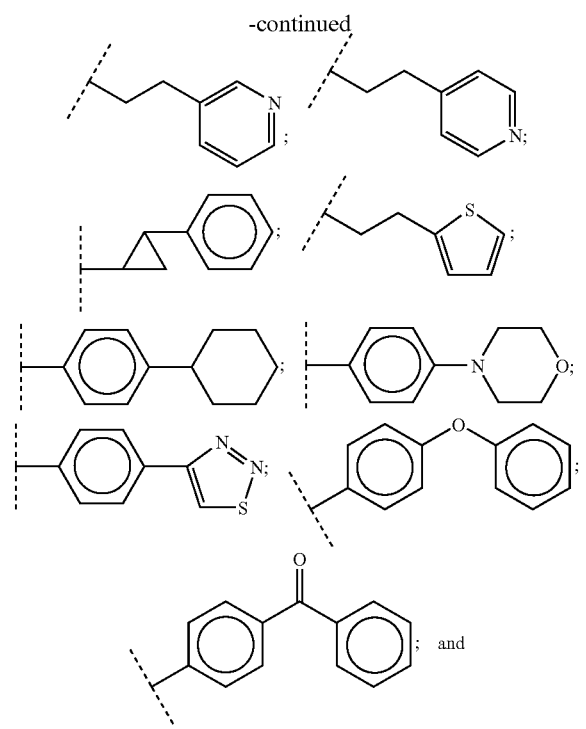
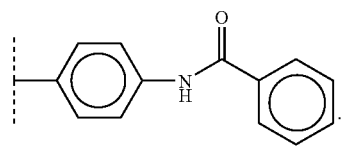

Particularly preferred compounds of the invention are compounds having the formula I″. Of compounds having the formula I″ those having the "cis/cis" configuration are particularly preferred.

Preferably, $R^4$ is a carboxylic acid, a salt or an ester thereof.

Different Forms of Compounds of Formula (I).

Compounds of formula (I) according to the invention can present themselves in different forms according to the solvent and the pH in which they are dissolved. For example, compound 1001 (Table 1, form 1) can exist in equilibrium with compound 2001 (see Table 2, hereinafter) and compound 3005 (Table 3) in form (3) when dissolved in phosphate buffer at pH 7.4. Without wishing to be bound by theory, it is believed that the predominant form in solution at pH 7.4 is represented by form (1).

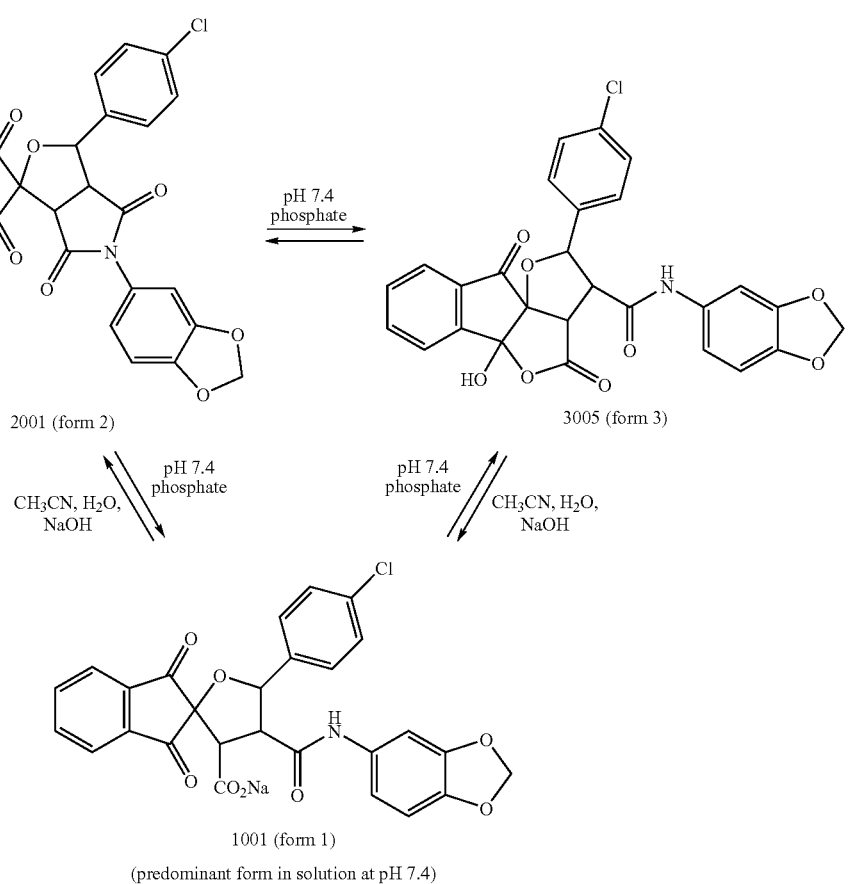

Specific Embodiments

Included within the scope of this invention are all compounds of formula formulae I, I', I'', I''', Ia, Ib, I,c, Id, Ie, If, Ig, or Ih, as presented in Tables 1 to 10 (with the exception of those compounds excluded by provisos).

Anti-papilloma Virus Activity

The antiviral activity of the compounds of formula (I) can be demonstrated by biochemical and biological procedures showing the inhibitory effect of the compounds on DNA replication.

Preferably, the compounds of formula (I) as described above are inhibitory against human papillomavirus (HPV). More preferably the compounds are active against HPV low risk or high risk type. Even more preferably, against low risk type HPV (i.e. type 6, type 11 and type 13, and especially HPV type 11). Alternatively, the high-risk type is selected from the group consisting of types 16, 18, 31, 33, 35, 45, 52, or 58, preferably, type 16). Most preferably, the compounds of the invention are directed against HPV types 6 and 11, even most preferably, against HPV-11.

A biochemical procedure for demonstrating anti-papilloma virus activity for the compounds of formula (I) is described in the examples hereinafter. This particular assay determines the ability of a test compound to inhibit the activity ($IC_{50}$) of HPV-11 DNA replication. More specifically, in the assay described herein, the inhibitory activity of the test compound is evaluated based on its ability to interfere with the E1-E2-DNA origin of replication interaction, thereby inhibiting initiation of viral DNA replication.

Methods for demonstrating the inhibitory effect of the compounds of formula (I) on papilloma viral replication involving in vitro assays are described in Examples 11 to 15 herein.

When a compound of formula (I), or one of its therapeutically acceptable salts, is employed as an antiviral agent, it may be administered orally, topically or systemically to mammals, e.g. humans, rabbits or mice, alone or in a vehicle comprising one or more pharmaceutically acceptable carriers, the proportion of which is determined by the solubility and chemical nature of the compound, chosen route of administration and standard biological practice.

Whether it be termed treatment or prophylaxis, a compound of formula (I) may also be used to prevent perinatal transmission of HPV from mother to baby, by administration to the mother prior to giving birth. More specifically, a compound of formula (I) may be used to prevent laryngeal papillomatosis in the baby.

For oral administration, the compound or a therapeutically acceptable salt thereof can be formulated in unit dosage forms such as capsules or tablets each containing a predetermined amount of the active ingredient, ranging from about 25 to 500 mg, in a pharmaceutically acceptable carrier.

For topical administration, the compound may be formulated in pharmaceutically accepted vehicles containing 0.1 to 5 percent, preferably 0.5 to 5 percent, of the active agent. Such formulations can be in the form of a solution, cream or lotion.

For parenteral administration, the compound of formula (I) may be administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula I is most desirably administered at a concentration level that will generally afford antivirally effective results without causing any harmful or deleterious side effects.

For oral administration, the compound or a therapeutically acceptable salt may be administered in the range of 10 to 200 mg per kilogram of body weight per day, with a preferred range of 25 to 150 mg per kilogram.

For topical application, the compound of formula (I) may be administered in a suitable formulation to the infected area of the body e.g. the skin, the genitalia, in an amount sufficient to cover the infected area. The treatment may be repeated, for example, every four to six hours until lesions heal.

For systemic administration, the compound of formula (I) may be administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

Although the formulations disclosed herein are indicated to be effective and relatively safe medications for treating papilloma viral infections, the possible concurrent administration of these formulations with other medications or agents to obtain beneficial results is also contemplated. Such other medications or agents include TCA, podophyllin, podofilox, Interferon or Imiquimod.

In addition to the above-mentioned antiviral agents, the compounds according to the invention may also be used post-cryotherapy or post-surgery or in combination with any other treatment for physically removing warts.

Methodology and Synthesis

The synthesis of compounds of formula I' is illustrated in Scheme I. The radicals Y, $R^3$ and $R^4$ are as defined previously:

Scheme I

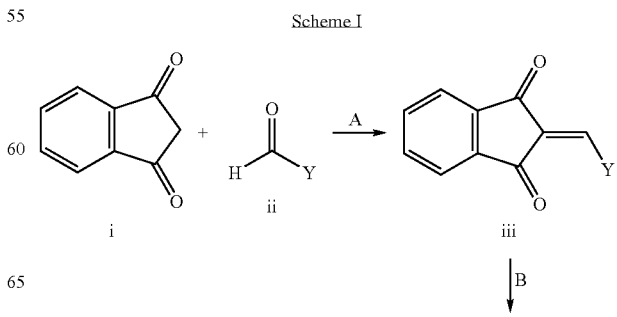

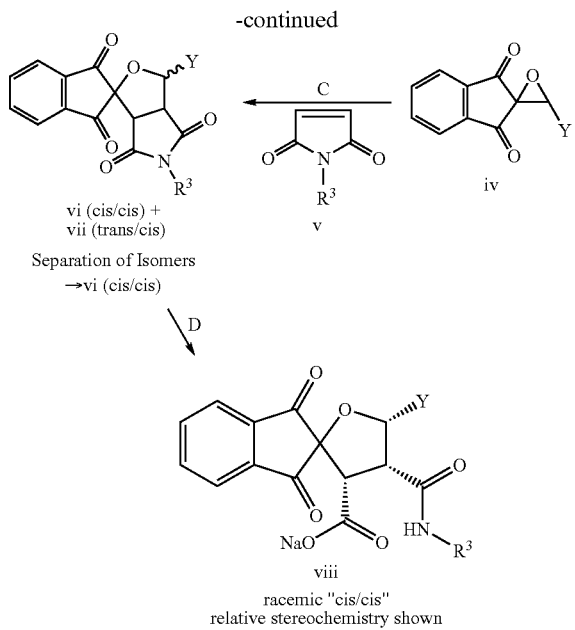

vi (cis/cis) +
vii (trans/cis)

Separation of Isomers
→vi (cis/cis)

racemic "cis/cis"
relative stereochemistry shown

A): Commercially available indan-1,3-dione (i) [or prepared according to known literature procedure: D. R. Bukle, N. J. Morgan, J. W. Ross, H. Smith, B. A. Spicer; J. Med. Chem. 1973, 16, 1334-1339] is condensed with aldehyde (ii) in a protic solvent (e.g. ethanol or propanol) in the presence of a catalytic amount of an organic amine (e.g. piperidine) to form the benzylidene (iii).

B): Benzylidene (iii) is converted to the epoxide (iv) by base-catalyzed oxidation with hydrogen peroxide in a protic solvent (such as methanol).

C): Epoxide (iv) undergoes thermal 1,3-dipolar cycloaddition in the presence of maleimide (v) at temperatures ranging from 80 to 100° C. in a solvent such as toluene or xylene (ref.: M. Y. Krysin, I. K. Anohina, L. P. Zalukaev; Khimiya Geterotsiklicheskikh Soedinenii, 1987, 11, 1463-1466). Thus racemic "cis/cis" (vi) and racemic "cis/trans" (vii) are obtained after purification (crystallization, flash column chromatography, or preparative HPLC). In general maleimides such as (v) are commercially available or alternatively can be easily prepared using literature procedures (e.g. P. Y. Reddy, S. Kondo, T. Toru, Y. Ueno; J. Org. Chem., 1997, 62, 2652-2654).

D): Racemic "cis/cis" compound (vi) is hydrolyzed to yield its opened carboxylate form (viii) also as "cis/trans" racemic mixture. Hydrolysis is achieved under aqueous basic conditions, such as aqueous sodium hydroxide and acetonitrile as a co-solvent.

Alternatively steps A) and B) can be carried out as a "one pot" reaction using an appropriate solvent (e.g. propanol) as described in Scheme II:

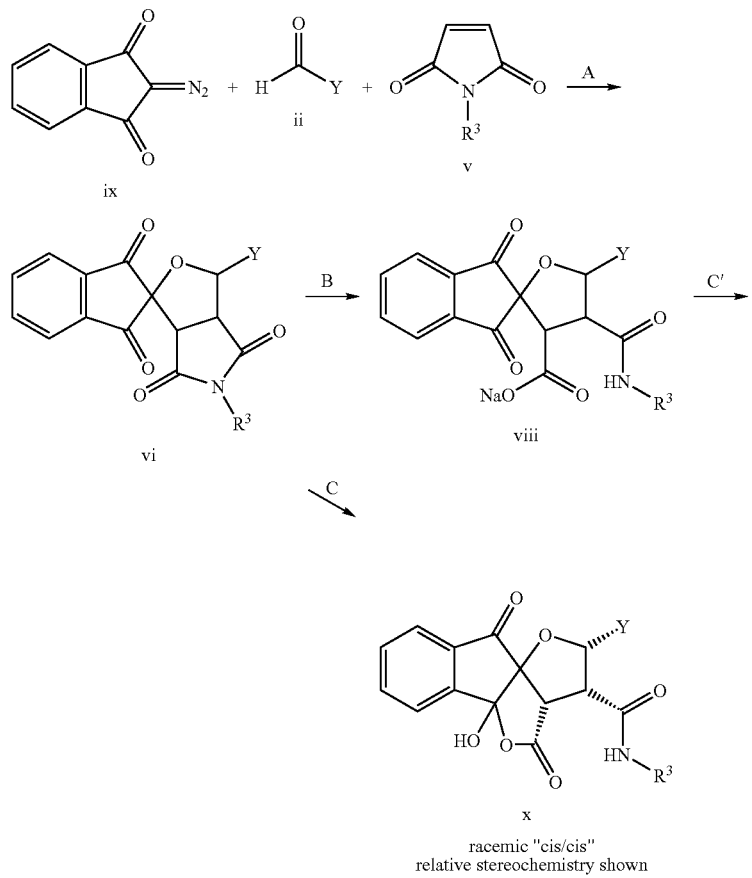

racemic "cis/cis"
relative stereochemistry shown

A): Diazoindan-1,3-dione (ix) [prepared according to literature procedure: J. Chem. Soc. Chem. Commun., 1990, 652-653] was reacted with aldehyde (ii) and maleimide (v) in the presence of a catalytic amount of rhodium(II) to give racemic "cis/cis" compound (vi).

B): The corresponding carboxylate (viii) is made following the hydrolysis procedure described in Scheme I, step D).

C) This step presents a further method for synthesizing compounds of formula I' in an alternative closed form. Racemic "cis/cis" compound (vi) is first hydrolyzed using procedure described in Scheme I, step D, followed with treatment with acid using dilute aqueous HCl to produce hydroxylactone (x) as racemic "cis/cis".

C') Alternatively the sodium salt intermediate (viii) is passed through a reverse phase column (HPLC) using a trifluoroacetic acid containing eluent to yield the hydroxylactone (x).

Compounds of formula I' wherein X and W form an epoxide are synthesized as illustrated in Scheme III:

Scheme III

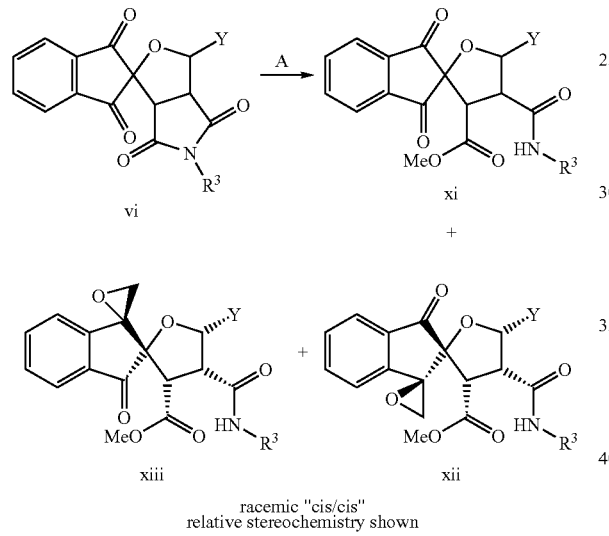

racemic "cis/cis"
relative stereochemistry shown

A): Racemic "cis/cis" compound (vi) is converted to the desired inhibitors via first hydrolysis under basic conditions, following by acidification and treatment with diazomethane. Compounds (xi), (xii) and (xiii) are separated from the mixture by flash chromatography or by preparative HPLC.

Scheme IV illustrates a general method for the synthesis of compounds of formula I' wherein X is H and W is hydroxy:

Scheme IV

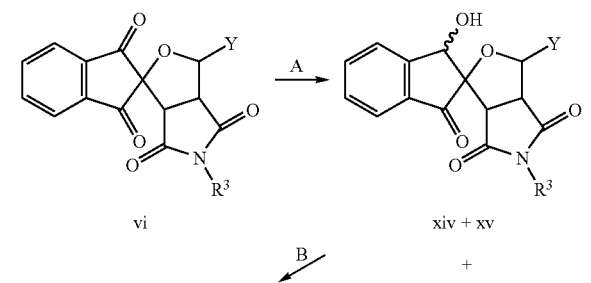

-continued

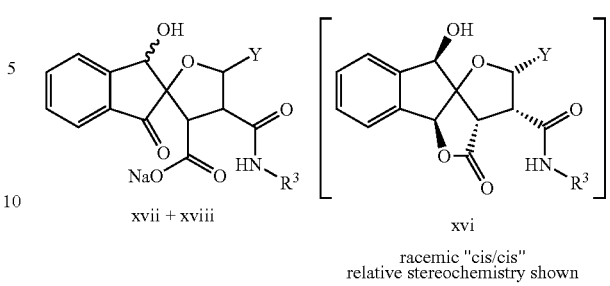

racemic "cis/cis"
relative stereochemistry shown

A): Reduction of racemic "cis/cis" compound (vi) is achieved using a hydride source (e.g. sodium borohydride) to give mixtures of the monohydroxy derivatives (xiv and xv) in addition to the hydroxy lactone (xvi) having the relative stereochemistry as shown.

B): After separation, racemic (xiv and xv) are hydrolyzed using the same procedure as in Scheme I, step D) to give racemic (xvii and xviii) after preparative separation.

Scheme V illustrates the method for synthesizing compounds of formula I' with the relative stereochemistry in trans/trans.

Scheme V

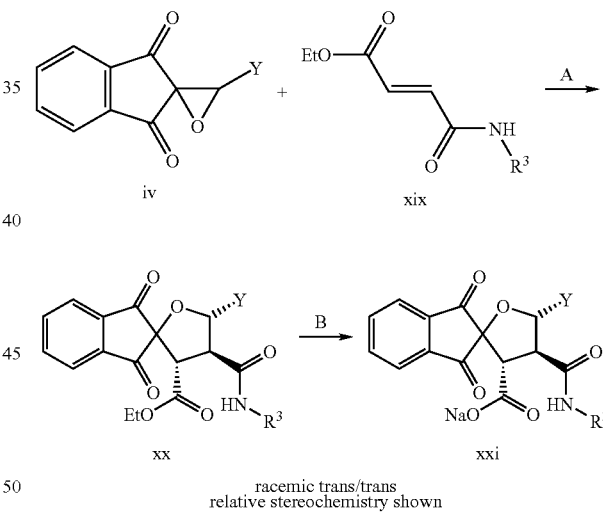

racemic trans/trans
relative stereochemistry shown

A): The amide (xix) obtained using literature procedure (ex: G. B. Villeneuve and T. H. Chan Tetrahedron Letters, 1997, 38, 6484) is reacted with epoxide (iv) in toluene under refluxing conditions to yield the cycloadduct ester (xx) as racemic trans/trans isomers.

B): Hydrolysis of the ester (xx) is done as described in Scheme I, step D) to give the desired carboxylate (xxi) also as racemic trans/trans isomers.

Compounds of formula I" and of formula I''', may be made in an analogous manner to those of formula I', except that instead of indan-1,3-dione as starting material, compound xxii is used.

Scheme VI

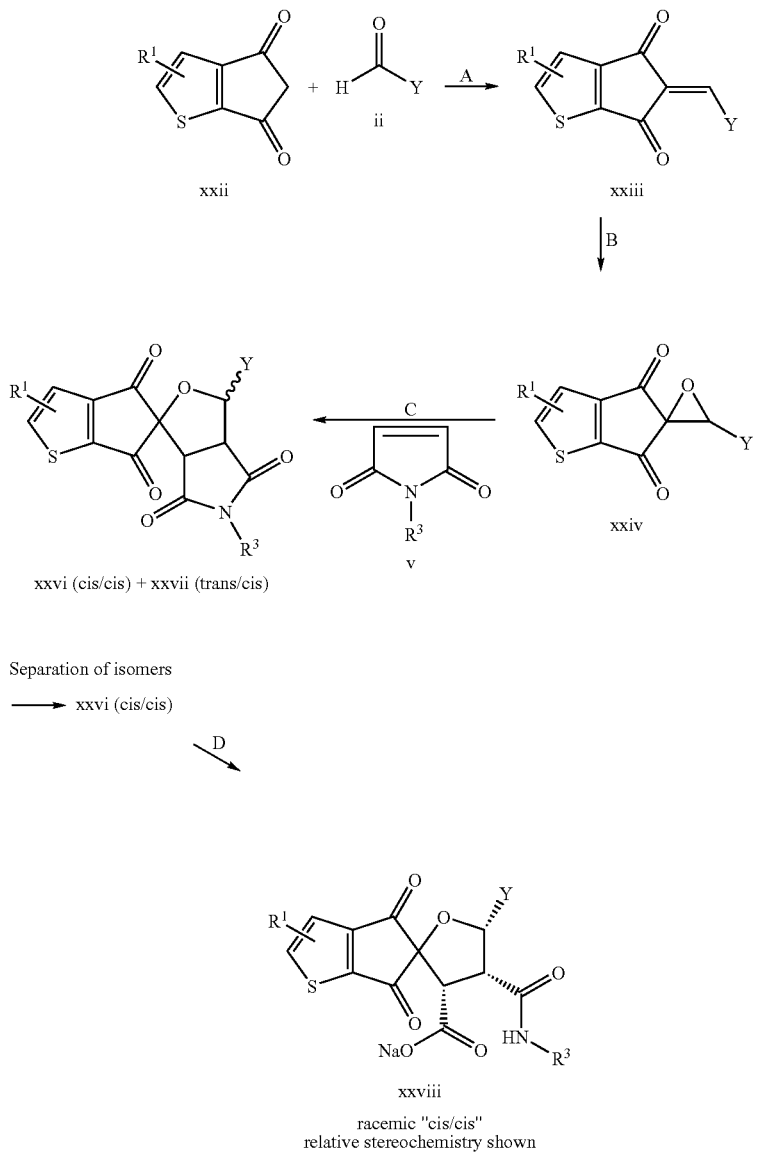

A): Compound(xxii) [prepared by homologation of commercially available 5-methyl-2-thiophenecarboxaldehyde with malonic acid, followed by reduction of the exocyclic double bond with sodium amalgam, or hydrogen over palladium, followed by cyclization with oxalyl chloride/ AlCl$_3$, or polyphosphoric acid, followed by oxidation with CrO$_3$/t-butylhydroperoxide] is condensed with aldehyde (ii) in a protic solvent (e.g. ethanol or propanol) in the presence of a catalytic amount of an organic amine (e.g. piperidine) to form the benzylidene (xxiii).

B): Benzylidene (xxiii) is converted to the epoxide (xxiv) by base-catalyzed oxidation with hydrogen peroxide in a protic solvent (such as methanol).

C): Epoxide (xxiv) undergoes thermal 1,3-dipolar cycloaddition in the presence of maleimide (v) at temperatures ranging from 80 to 100° C. in a solvent such as toluene or xylene (ref.: M. Y. Krysin, I. K. Anohina, L. P. Zalukaev; Khimiya Geterotsiklicheskikh Soedinenii, 1987, 11, 1463-1466). Thus racemic "cis/cis" (xxvi) and racemic "cis/trans" (xxvii) are obtained after purification (crystallization, flash column chromatography, or preparative HPLC). In general maleimides such as (v) are commercially available or alternatively can be easily prepared using literature procedures (e.g. P. Y. Reddy, S. Kondo, T. Toru, Y. Ueno; J. Org. Chem., 1997, 62, 2652-2654).

D): Racemic "cis/cis" compound (xxvi) is hydrolyzed to yield its opened carboxylate form (xxviii) also as "cis/cis" racemic mixture. Hydrolysis is achieved under aqueous basic conditions, such as aqueous sodium hydroxide and acetonitrile as a co-solvent.

An alternate route to compounds of the formula I" is shown in Scheme VII.

Scheme VII

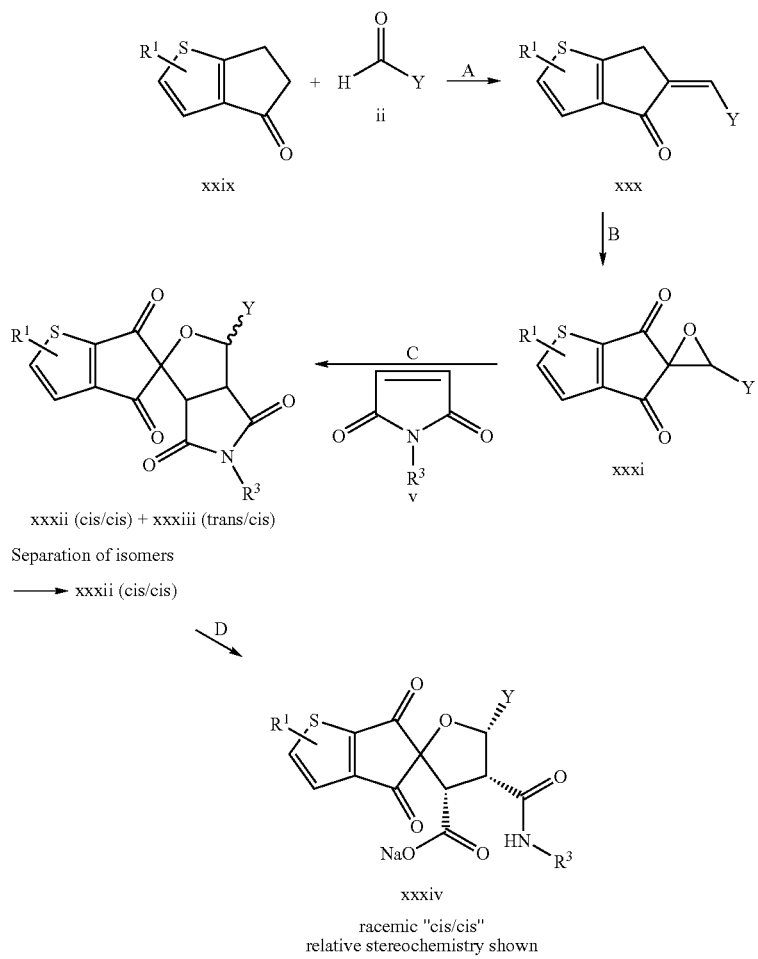

xxxii (cis/cis) + xxxiii (trans/cis)

Separation of isomers

⟶ xxxii (cis/cis)

↓ D xxxiv
racemic "cis/cis"
relative stereochemistry shown

A) Compound xxix [prepared by homologation of commercially available 5-methyl-2-thiophenecarboxaldehyde with malonic acid, followed by reduction of the exocyclic double bond with sodium amalgam, or hydrogen over palladium, followed by cyclization with oxalyl chloride/ $AlCl_3$, or polyphosphoric acid] is condensed with aldehyde (ii) in the presence of a catalytic amount of an acid catalyst (e.g. p-toluene sulfonic acid) in benzene or toluene, to form the benzylidene (xxx).

B) Benzylidene (xxx) is converted to the epoxide (xxxi) by oxidation (e.g. $CrO_3$/t-butylhydroperoxide)

C) Epoxide (xxxi) undergoes thermal 1,3-dipolar cycloaddition in the presence of maleimide (v) at temperatures ranging from 80 to 100° C. in a solvent such as toluene or xylene (ref.: M. Y. Krysin, I. K. Anohina, L. P. Zalukaev; Khimiya Geterotsiklicheskikh Soedinenii, 1987, 11, 1463-1466). Thus racemic "cis/cis" (xxxii) and racemic "cis/trans" (xxxiii) are obtained after purification (crystallization, flash column chromatography, or preparative HPLC). In general maleimides such as (v) are commercially available or alternatively can be easily prepared using literature procedures (e.g. P. Y. Reddy, S. Kondo, T. Toru, Y. Ueno; J. Org. Chem., 1997, 62, 2652-2654).

D) Racemic "cis/cis" compound (xxxii) is hydrolyzed to yield its opened carboxylate form (xxxiv) also as "cis/cis" racemic mixture. Hydrolysis is achieved under aqueous basic conditions, such as aqueous sodium hydroxide and acetonitrile as a co-solvent.

EXAMPLES

The present invention is illustrated in further detail by the following non-limiting examples. All reactions were performed in a nitrogen or argon atmosphere. Temperatures are given in degrees Celsius. Solution percentages or ratios express a volume to volume relationship, unless stated otherwise.

Abbreviations or symbols used herein include:
DEAD: diethyl azodicarboxylate;
DIEA: diisopropylethylamine;
DMAP: 4-(dimethylamino)pyridine;
DMSO: dimethylsulfoxide;
DMF: dimethylformamide;
ES MS: electron spray mass spectrometry;
Et: ethyl;
EtOAc: ethyl acetate;
$Et_2O$: diethyl ether;

HPLC: high performance liquid chromatography;
iPr: isopropyl
Me: methyl;
MeOH: methanol;
MeCN: acetonitrile;
Ph: phenyl;
TBE: tris-borate-EDTA;
TBTU: 2-(1H-benzotriazol-1-yl)-N,N,N',N'-tetramethyluronium tetrafluoroborate;
TFA: trifluoroacetic acid;
THF: tetrahydrofuran;
MS (FAB) or FAB/MS: fast atom bombardment mass spectrometry;
HRMS: high resolution mass spectrometry;

Example 1

Preparation of Compounds 2013 (Table 2) and 1002 (Table 1)

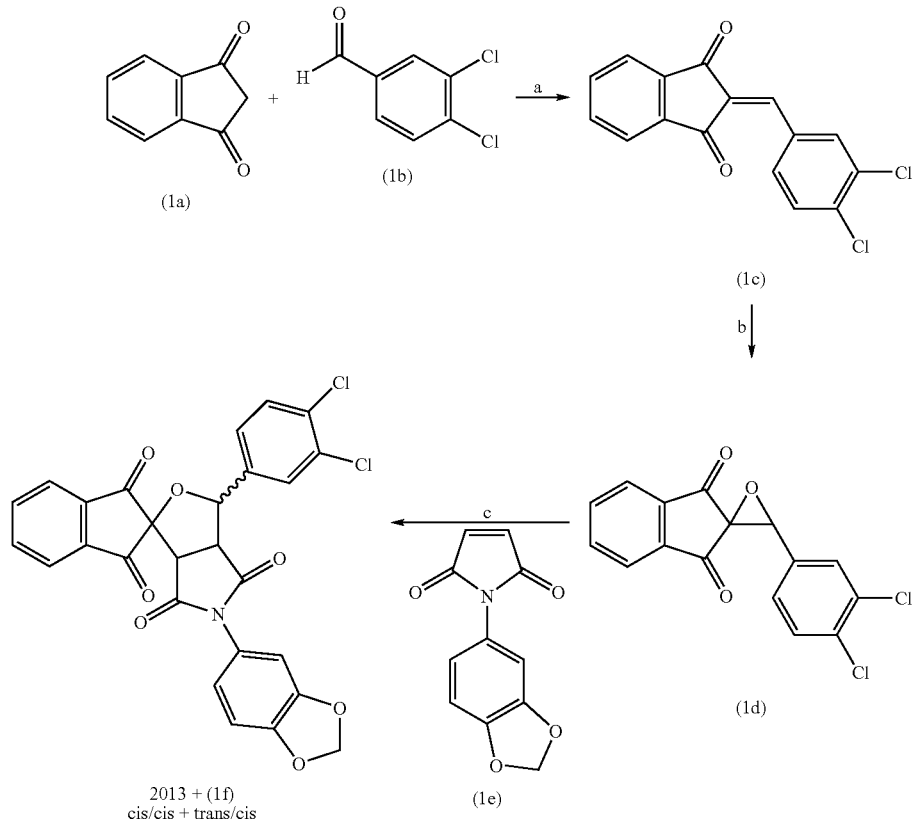

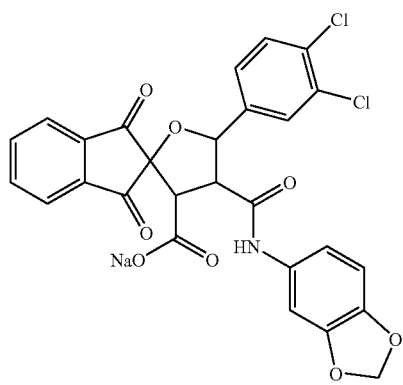

1002
racemic cis/cis

Step a:

To a solution of indan-1,3-dione (1a) (960 mg, 6.6 mmol) in EtOH (8.2 mL) was added 3,4-dichlorobenzaldehyde (1b) (1.3 g, 7.2 mmol) followed by piperidine (3 drops). The reaction mixture was heated to reflux for 30 min. After cooling, the reaction was diluted with EtOH (8 mL) and the precipitate was filtered. The resulting solid was triturated twice with EtOH and dried under high vacuum to give 2-(3,4-dichloro-benzylidene)-indane-1,3-dione (1c) (1.7 g, 82% yield).

Step b:

To a suspension of 2-(3,4-dichloro-benzylidene)-indane-1,3-dione (1c) (1.6 g, 5.2 mmol) in MeOH (13 mL) was added hydrogen peroxide (30% solution, 3 mL). The mixture was cooled to 0° C. and sodium hydroxide (1N, 300 μL) was added dropwise. After addition was completed, stirring was continued at room temperature for 1 h. The mixture was then poured into water (5 mL) and the resulting solid was collected by filtration and washed with water and MeOH. After drying under high vacuum 3-(3,4-dichlorophenyl)-spiro (oxirane-2,2'-indan)-1',3'-dione (1d) (1.6 g, 95% yield) was obtained.

Step c: Compound 2013

A mixture of 3-(3,4-dichlorophenyl)-spiro (oxirane-2,2'-indan)-1',3'-dione (1d) (11 g, 33,4 mmol) and 1-benzo (1,3) dioxol-5-yl-pyrrol-2,5-dione (1e) (7.3 g, 33.4 mmol) in toluene (167 mL) was heated to reflux for 16 h. After cooling and concentration, the residue was purified by flash chromatography (SiO$_2$, gradient 50% EtOAc/hexane to 30% hexane/EtOAc) to give compound 2013 (Table 2) (cis/cis isomer, 17.9 g, 50% yield) and (1f) (trans/cis isomer, 4.1 g, 23% yield).

Step d: Compound 1002

To a solution of (2013) (143 mg, 0.27 mmol) in CH$_3$CN (27 mL) was added NaOH (0.02N, 135 mL, 0.27 mmol) using a syringe pump over 1 h. After the addition was completed, the reaction mixture was stirred for an extra 2 h and the resulting solution was concentrated and lyophilized to give compound 1002 (Table 1) (161 mg, 100% yield) as a white solid.

Example 2

Preparation of Compound 4003 (Table 4)

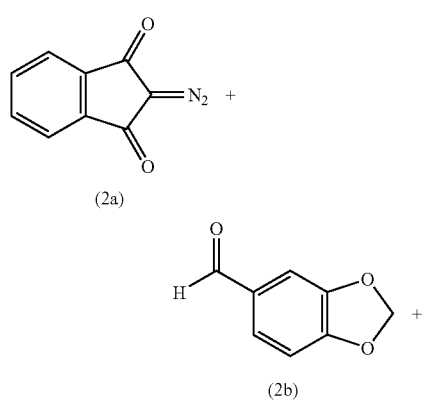

Preparation of Compound (2a):

To a suspension of sodium azide (2.4 g, 36.3 mmol) in CH$_3$CN (73 mL) was added methanesulfonyl chloride (2.8 mL, 36.3 mmol). After stirring for 16 h, the reaction mixture was poured over a suspension of indan-1,3-dione (5.3 g, 36.3 mmol) and cesium carbonate (11.8 g, 36.3 mmol) in CH$_3$CN (50 mL). The mixture was stirred until reaction was complete (2 h), and then filtered through Celite. The filter cake was washed with EtOAc and the organic solvents were removed in vacuo. The resulting gum was diluted with EtOAc and rinsed successively with NaOH (1N), H$_2$O and brine. The organic layer was dried (MgSO$_4$), evaporated and the crude oil purified by flash chromatography (SiO$_2$, 50% hexane/EtOAc) to give 2-diazoindan-1,3-dione (2a) (2.6 g, 42% yield).

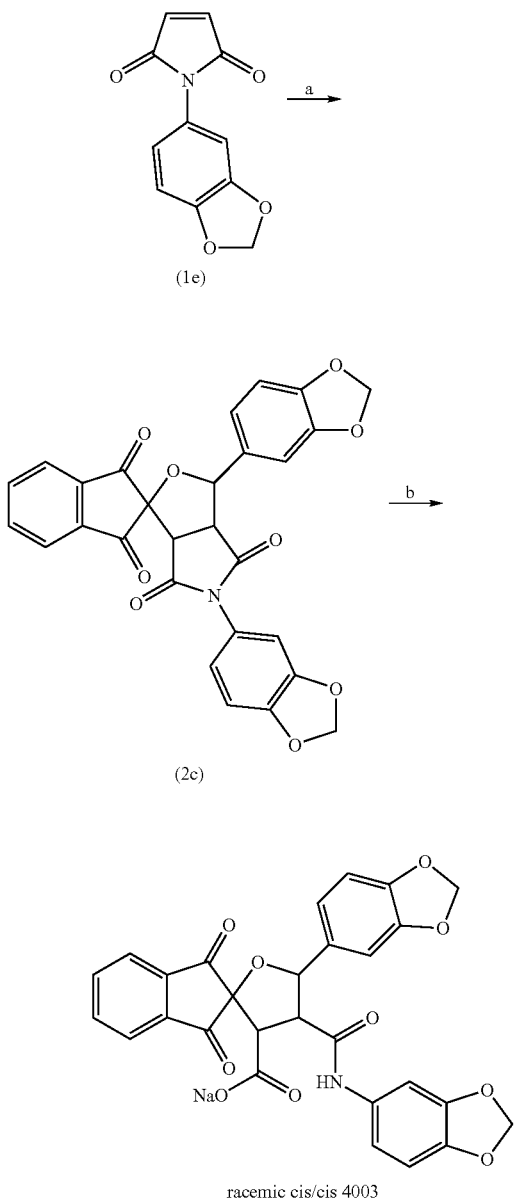

Step a:

To a mixture of diazoindan-1,3-dione (2a) (317 mg, 1.8 mmol), piperonal (2b) (553 mg, 3.7 mmol) and 1-benzo (1,3) dioxol-5-yl-pyrrol-2,5-dione (1e) (400 mg, 1.8 mmol) in benzene (6 mL) and Rh$_2$(OAc)$_4$ (4.5 mg) were added and heated to reflux for 1 h. After cooling and concentrating, the reaction mixture was purified by flash chromatography (SiO$_2$, gradient 50% hexane/EtOAc to 30% hexane/EtOAc) to give the desired compound (2c) as beige solid (76.5 mg, 8% yield).

Step b: Compound 4003

Following the same procedure as in Example 1, step d, compound 4003 was obtained as a white solid.

Example 3

Preparation of Compound 3009 (Table 3)

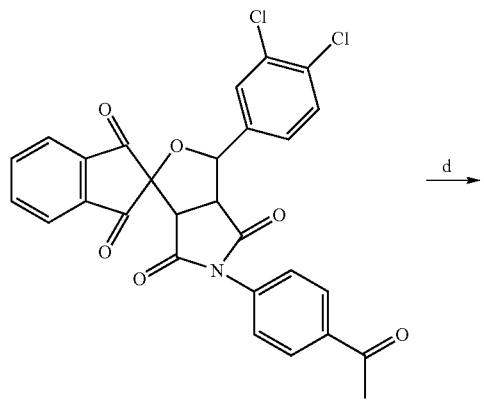

racemic cis/cis 2016

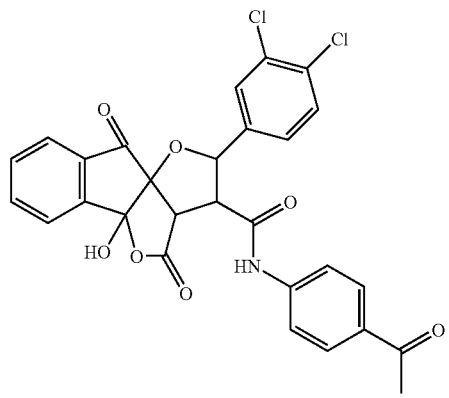

racemic cis/cis 3009

Compound 2016 was prepared as described in Example 1, steps a to c using N-(4-acetylphenyl)maleimide in the cycloaddition (step c) to give a white solid in 40% yield.

Step d:

To a solution of 2016 (100 mg, 0.19 mmol) in CH$_3$CN was added NaOH (0.02 N, 9.4 mL, 0.19 mmol) over 1 h using a syringe pump. After addition was complete, the solution was concentrated and lyophilized to give a white solid which was purified on reverse phase HPLC using a gradient of CH$_3$CN/H$_2$O containing TFA (0.06%). After collecting the desired fractions and lyophilization compound 3009 was obtained (43 mg, 42% yield) as a white solid.

Example 4

Preparation of Compound 1022 (Table 1) and Compound 7001 (Table 7)

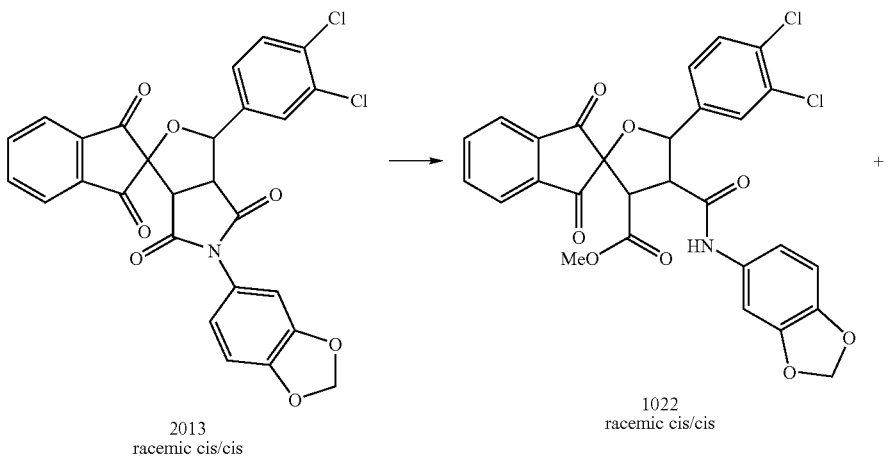

2013
racemic cis/cis 1022
racemic cis/cis

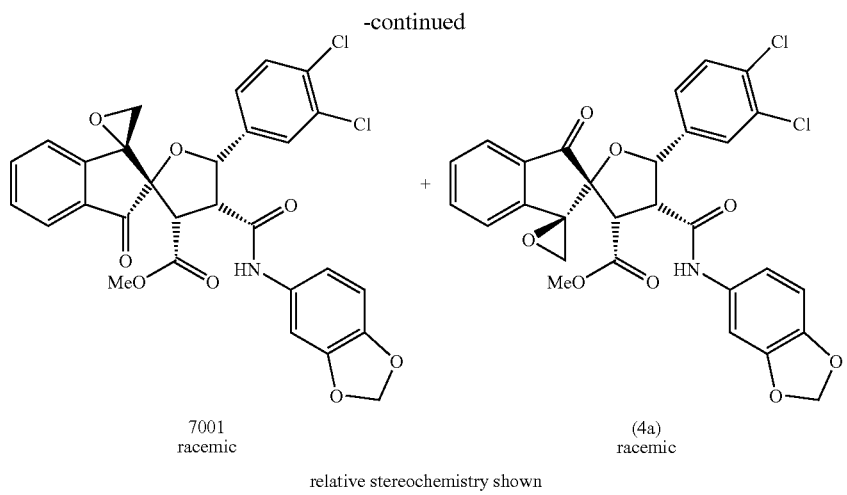

7001
racemic (4a)
racemic relative stereochemistry shown

To a solution of 2013 (racemic) (143 mg, 0.27 mmol) in CH$_3$CN (27 mL) was added NaOH (0.02N, 135 mL, 0.27 mmol) using a syringe pump over 1 h. After addition was complete, the reaction mixture was concentrated. To the aqueous layer was added HCl (1N, 1 mL) and the resulting acidic layer was extracted twice with EtOAc. The combined organic layer was washed with H$_2$O and brine, dried (MgSO$_4$) and filtered. To the filtrate was added a solution of CH$_2$N$_2$ in Et$_2$O (excess) and the mixture was evaporated to dryness. The resulting crude compound was purified by preparative HPLC using a gradient of CH$_3$CN/H$_2$O containing TFA (0.06%). After collecting and lyophilizing the desired fractions, compounds 1022 (11 mg, 12% yield), (4a) (9 mg, 10% yield), and 7001 (47 mg, 26% yield) as racemic mixtures were obtained as white solids.

Example 5

Preparation of Compound 8001

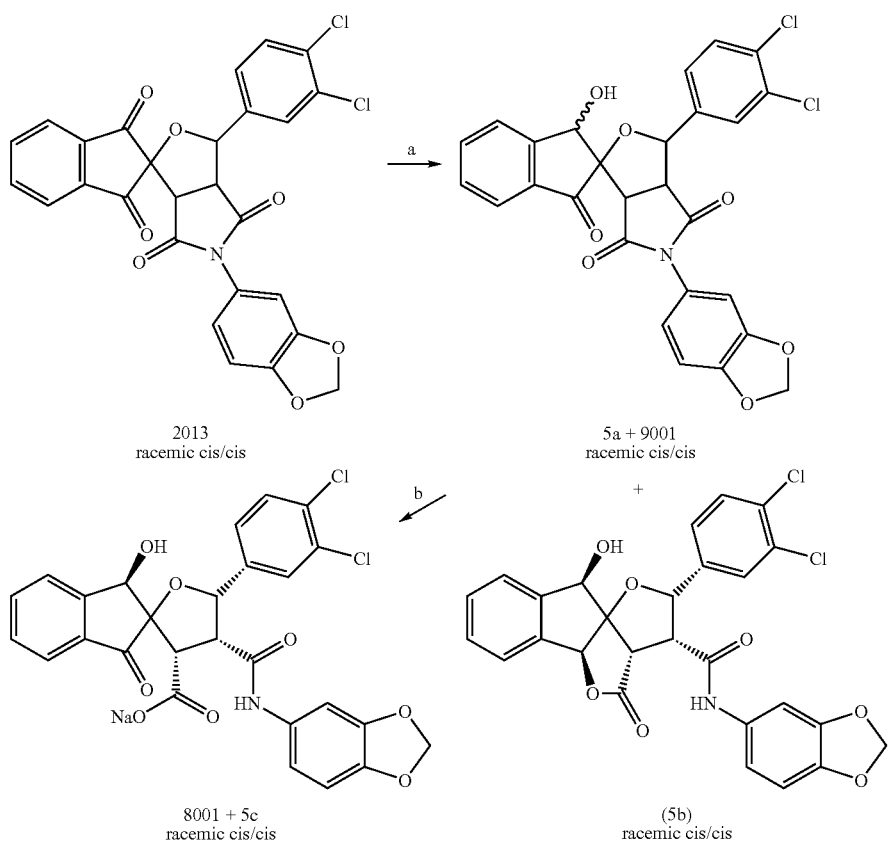

2013
racemic cis/cis

5a + 9001
racemic cis/cis

8001 + 5c
racemic cis/cis (5b)
racemic cis/cis relative stereochemistry shown

Step a:

To a solution of 2013 (racemic) (500 mg, 0.93 mmol) in THF/MeOH mixture (20/5 mL) cooled at 0° C. was added $NaBH_4$ (35 mg, 0.93 mmol). After stirring for 30 min, the reaction was quenched with aqueous citric acid solution (10%) and diluted with EtOAc. The aqueous layer was extracted twice with EtOAc and the combined organic layers were washed with brine, dried ($MgSO_4$), filtered and concentrated. Preparative HPLC gave racemic alcohols (5a)+9001 (360 mg, 72% yield, retention times: 14.1 and 12.4 min) as well as hydroxylactone (5b) (95 mg, 18% yield, retention time: 13.8 min).

The mixture of alcohols was separated by preparative HPLC to generate the two isomeric compounds as white solids:

Step b:

To the mixture of alcohols (5a)+9001 (2:1 ratio, 36 mg, 0.07 mmol) in $CH_3CN$ (10 mL) was added NaOH (0.02N, 3.4 mL, 0.07 mmol) over 2 h using a syringe pump. The $CH_3CN$ was evaporated and the residue was purified by preparative HPLC. The desired fractions were lyophilized and the resulting solids were retreated with NaOH (1 equiv.) and lyophilized to give compound 8001 (21.3 mg, 59% yield, retention time: 13.7 min) and (5c) (6.0 mg, 17% yield, retention time: 10.9 min) as white solids.

Example 6

Preparation of Compound 5001 (Table 5)

Preparation of Amide (6a):

A mixture of monoethyl fumarate (1 g, 6.9 mmol) and hexachloroacetone (0.5 mL, 3.5 mmol) in $CH_2Cl_2$ (13 mL) was stirred under nitrogen and cooled to −78° C. Triphenylphosphine (1.8 g, 6.9 mmol) in $CH_2Cl_2$ (6.9 mL) was added dropwise and the mixture was stirred for 20 min. The acyl chloride solution was then treated with a solution of 3,4-methylenedioxyaniline (946 mg, 6.9 mmol) in $CH_2Cl_2$ (6.9 mL) followed by $Et_3N$ (0.96 mL, 6.9 mmol) in $CH_2Cl_2$ (6.9 mL). The reaction mixture was allowed to warm to room temperature after which the solvent was removed under high vacuum. The resulting residue was purified by flash chromatography ($SiO_2$, 20% EtOAc/hexane to give the desired amide (6a) (961 mg, 53% yield) as an orange solid.

Step a:

Amide (6a) was reacted with epoxide (Id) using the same procedure as in Example 1, step c to give ester (6b) (77 mg, 14% yield) as an orange solid.

Step b:

Using the same procedure as in Example 1, step d, compound 5001 was obtained as a white solid (8 mg, 25% yield).

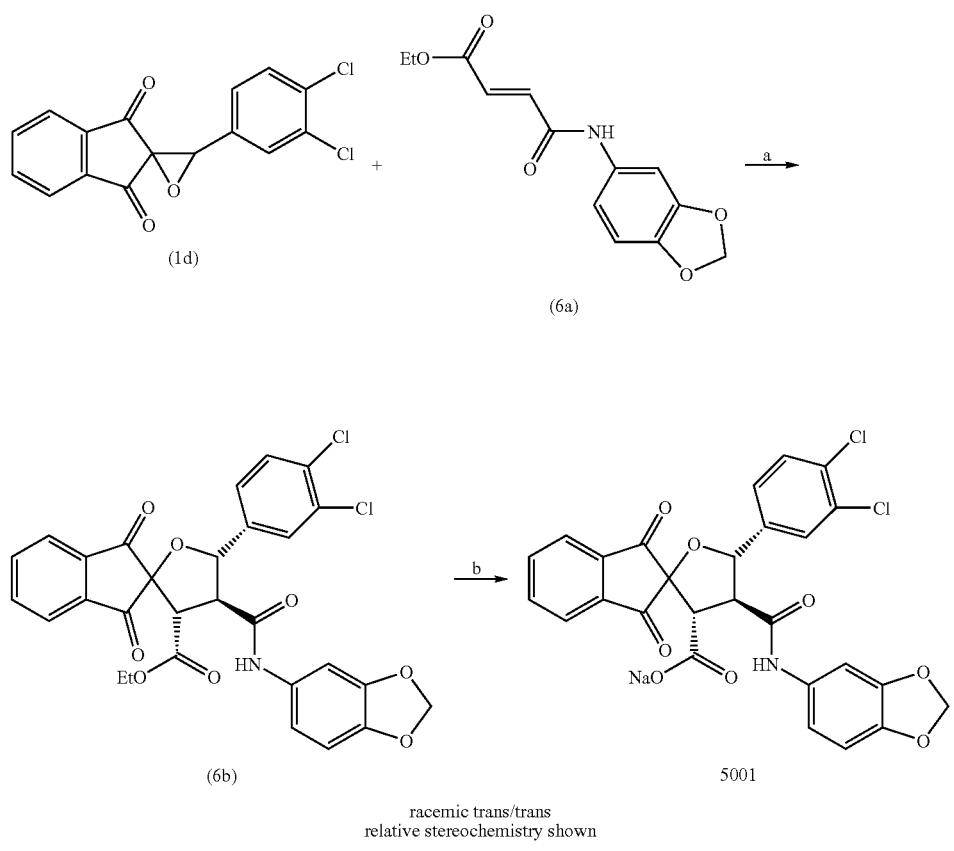

racemic trans/trans
relative stereochemistry shown

Example 7
Preparation of Compound 4005 (Table 4)
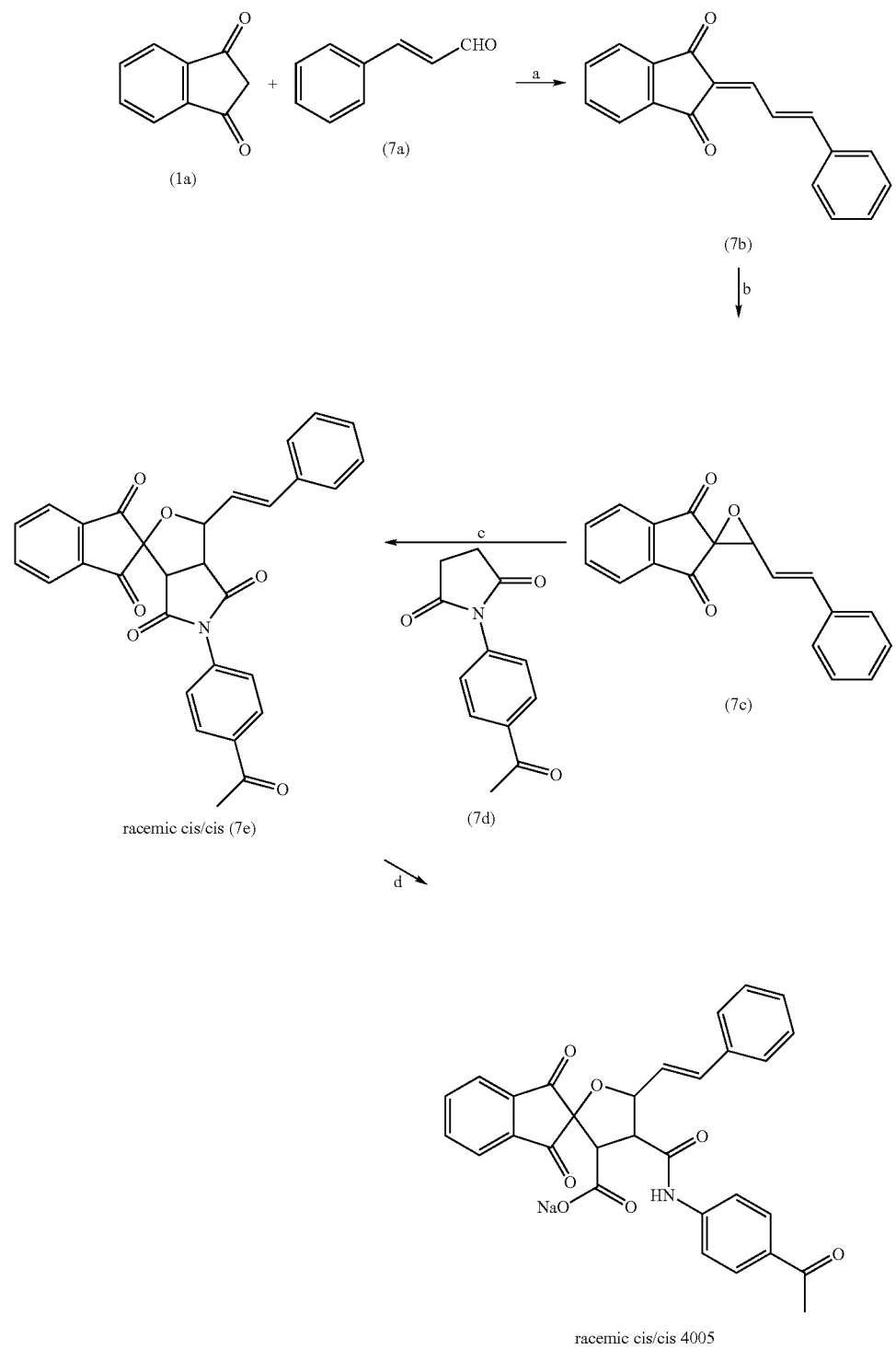

Step a:

The same procedure as in Example 1, step a, was followed but using indan-1,3-dione and trans-cinnamaldehyde (7a) as starting material, to give compound (7b) after purification (11% yield) as an orange solid.

Steps b & c:

The same procedures as in Example 1, steps b and C were used but using N-(n-acetylphenyl)maleimide (7d) in the cycloaddition (step c) to afford compound (7e) (38% yield) as a white solid.

Hydrolysis was achieved as described in Example 1, step d, to give compound 4005 (racemic) (50% yield) as a white solid.

Example 8

Preparation of Compound #D1002 (Table 1D)

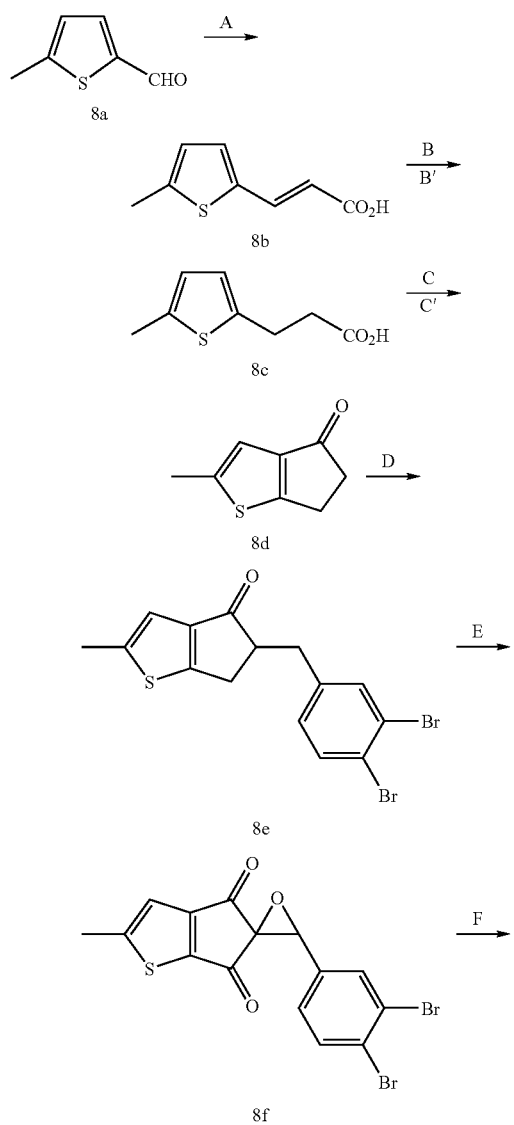

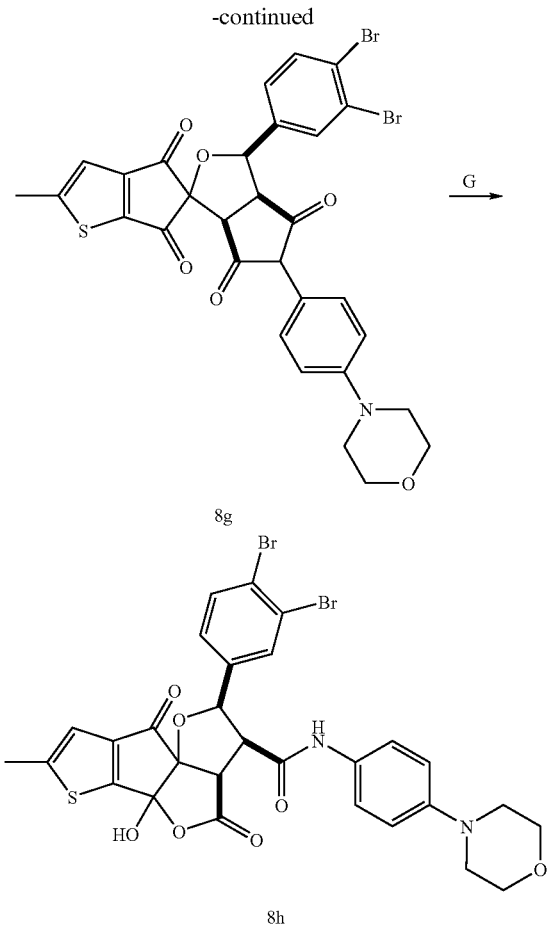

A: A solution of 8a (9.5 g, 75.4 mmol), malonic acid (15.7 g, 151 mmol) and piperidine (1.3 mL) in pyridine (40 mL) was refluxed overnight. The resulting mixture was allowed to cool to room temperature whereupon water (200 mL) was added. The mixture was acidified by the addition of concentrated HCl and allowed to stir for 1 h. The mixture was filtered and the solid washed with water. Drying under vacuum gave 8b as a yellow powder (12.8 g, 100%).

B: To a vigorously stirred solution of 8b (5.9 g, 35 mmol) and 1 N NaOH (46 mL, 46 mmol) in water (40 mL) was added 2% sodium amalgam (82 g, 105 mmol) in small portions over 1 h. After complete addition the mixture was stirred for a further hour. Mercury was removed by decanting and the aqueous solution was acidified with concentrated HCl. Solid NaCl was added to saturation and the resulting mixture was extracted with ether, The combined etherial extracts were washed with brine and dried over $MgSO_4$. Removal of solvent under reduced pressure gave 8c as a brown solid (3.72 g, 62%).

B: Alternatively, a slurry of 8b (7.5 g, 44.6 mmol) and $Pd(OH)_2$ (500 mg) in ethanol was stirred under an atmosphere of hydrogen for 18 h. Filtering through glass microfibre and removal of solvent gave 3 as a white solid (7.0 g, 93%).

C: To a solution of 8c (1.75 g, 10.3 mmol) and oxalyl chloride (1.35 mL, 15.4 mmol) in $CH_2Cl_2$ (50 mL) was added one drop of DMF. The resulting solution reduced pressure and the resulting residue dissolved in $CS_2$ (50 mL). Solid $AlCl_3$ (2.05 g, 15.4 mmol) was then introduced and the resulting mixture refluxed overnight. Ice (80 g) was then added followed by concentrated HCl (30 mL) and the resulting mixture was stirred for 30 min. Extraction with CH$_2$Cl$_2$ was followed by washing with 1N NaOH, brine and drying (MgSO$_4$). Flash chromatography (20% EtOAc in hexanes) gave 8d (272 mg, 17%) as a yellow solid.

C': Alternatively, solid 8c (1.0 g, 5.88 mmol) was added in small portions to warm (75° C.) polyphosphoric acid (8.5 g). Heating was continued at 75° C. for one hour after the addition was complete. Cooling to room temperature was followed by dilution with water and extraction with CH$_2$Cl$_2$ (3×). The combined organics were dried over MgSO$_4$ and concentrated. Flash chromatography (50% EtOAc in hexanes) gave 8d as a white solid (0.31 g, 35%).

D: A solution of 8d (1.06 g, 6.97 mmol), 3,4-dibromobenzaldehyde (1.84 g, 6.97 mmol) and p-toluenesulfonic acid (100 mg) in benzene (25 mL) was refluxed for 24 h with azeotropic removal of water. Upon cooling and addition of ether (25 mL) a solid precipitated which was filtered to give 8e as a tan solid (1.35 g, 49%).

E: To a solution of CrO$_3$ (50 mg, 0.50 mmol) in CH$_2$Cl$_2$ (15 mL) was added tert-butylhydroperoxide (2.6 mL of a 70% solution in water). After stirring for 2 minutes, 8e (1.0 g, 2.51 mmol) was added. After stirring for 18 h at room temperature the solution was diluted with CH$_2$Cl$_2$ and water and extracted three times with small portions of CH$_2$Cl$_2$. The combined organics were dried over MgSO$_4$ and concentrated in vacuo. Trituration of the resulting solid with ether gave 0.61 g (60%) of a solid diketone.

The material so obtained (0.45 g) was dissolved in EtOH (15 mL) to which was added 30% H$_2$O$_2$ (0.38 mL) and one drop of 1N NaOH. After stirring for 3 h the solution was filtered to give 8f as a yellow solid (421 mg, 90%).

F: A solution of 8f (0.30 g, 0.70 mmol) and N-[4-(N'-morpholino)phenyl]maleimide (0.18 g, 0.70 mmol) in toluene (8 mL) was refluxed for 48 h. After cooling to room temperature a solid formed was filtered and then triturated with THF to provide 8g (75 mg, 16%). G: To a solution of 8g (69 mg, 0.10 mmol) in 40% THF:CH$_3$CN (8 mL) was added NaOH (5.3 mL of a 0.02 M solution in water) over 10 h via syringe pump. The reaction mixture was purified directly by preparative HPLC (Chiralcel OD column, isocratic 50% CH$_3$CN/H$_2$O, 0.06% TFA) which afforded enantiomerically pure 8h (2.5 mg, 4%).

Example 9

Preparation of 5-Methyl-6-Fluoro-1,3-Indanedione

This material is useful as a starting material for preparation of compounds of the formula I' in which R$^1$ is c-F and b-Me.

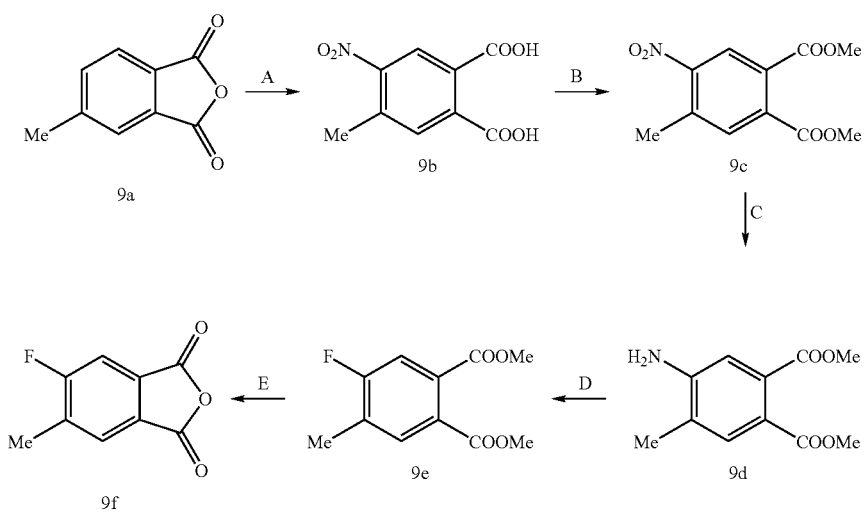

a) HNO$_3$, H$_2$SO$_4$; b) (MeO)$_2$SO$_2$, K$_2$CO$_3$, DMF; c) H$_2$, Pd(OH)$_2$/C; d) NaNO$_2$, HF$_x$·Pyr; NaH, EtOAc, then H$_3$O$^+$ A, B: 4-Methylphthalic anhydride 9a (67.5 mmol, 10.94 g) and concentrated sulfuric acid (10 mL) were placed in a three-necked round-bottomed flask and the mixture was stirred mechanically at 80° C. A mixture of fuming nitric acid (d=1.5, 4.2 mL) and concentrated sulfuric acid (3.0 mL) was added slowly from a dropping funnel at such a rate as to maintain the temperature of the stirred mixture at 100-110° C. Then concentrated nitric acid (d=1.42, 18 mL) was added as rapidly as possible without causing the temperature to rise above 110° C. The reaction mixture was heated at 100° C. for two hours, allowed to stand at room temperature for 16 h and poured into 30 mL of water. The white precipitate was filtered off and the filtrate was extracted with ethyl ether. The organic phase was dried with magnesium sulfate, filtered and concentrated under vacuum. The residual solid (13 g) was dissolved in N,N-dimethylformamide (50 mL) containing potassium carbonate (0.12 mol, 16.9 g). Dimethyl sulfate (0.12 mol, 15.4 g, 11.5 mL) was added and the mixture was stirred magnetically at room temperature for two hours. N,N-dimethylformamide was evaporated under reduced pressure. The residue was dissolved in ethyl acetate and the organic phase was washed with water, brine and dried with magnesium sulfate. The salts were filtered off and the filtrate was concentrated under vacuum. The residue was purified by flash chromatography on type H silica gel using hexane/ethyl acetate (4/1) as eluent to yield 5.26 g (31%) of dimethyl 4-methyl-5-nitrophthalate 9c as a white solid.

C: Dimethyl 4-methyl-5-nitrophthalate 9c (3.41 g, 13.5 mmol) was dissolved in a mixture of methanol (120 mL) and tetrahydrofuran (20 mL). Palladium hydroxide on carbon (20%, 300 mg) was added and the suspension was stirred magnetically at room temperature under hydrogen atmosphere (1 atm) for 16 hours. The reaction mixture was filtered on Celite and the filtrate was concentrated under vacuum. The residual oil was purified by flash chromatography on type H silica gel using hexane/ethyl acetate (2/1) as eluent, followed by hexane/ethyl acetate (1/1), to give 2.88 g (96%) of a colorless oil which corresponded to dimethyl 4-methyl-5-aminophthalate 9d.

D: A teflon reactor was charged with dimethyl 4-methyl-5-aminophthalate 9d (4.53 g, 20.3 mmol). HF.pyridine (50 mL, ca 1.7 mol HF) was added. The reaction mixture was stirred for 5 min at 0° C. and sodium nitrite (1.55 g, 22.5 mmol) was added to produce a purple solution. The mixture was stirred for 15 min at room temperature and for 30 min at 120° C. The reaction mixture was poured onto ice and 4 N sodium hydroxide. Ethyl acetate was added and the mixture was filtered. The organic phase was dried with magnesium sulfate, filtered, washed with 1 M aq HCl, dried again with magnesium sulfate, filtered and concentrated under vacuum. The residual red liquid was purified by flash chromatography on type H silica gel using hexane/ethyl acetate (4/1) as eluent to give 1.54 g (33%) of dimethyl 4-methyl-5-fluorophthalate 9e as a white solid.

E: Dimethyl 4-methyl-5-fluorophthalate 9e (1.65 g, 7.29 mmol) was dissolved in anhydrous ethyl acetate (4 mL). Sodium hydride (348 mg, 14.5 mmol) was added and the mixture was heated at 100° C. for 4 hours. The reaction mixture was cooled to room temperature and a mixture containing 10 mL of hexane and 6 mL of ethyl ether/ethanol (1/1) was added. The yellow precipitate was triturated for 5 min, filtered and dried under vacuum. The yellow solid (1.07 g) was then suspended in a solution containing water (22 mL) and concentrated hydrochloric acid (2.2 mL) and the suspension was heated for 17 min at 80° C. The mixture was then lyophilized to give 810 mg (62%) of 5-methyl-6-fluoro-1,3-indandione 9f as a beige solid.

Examples of compounds made using 5-methyl-6-fluoro-1,3-indandione are compounds #A1015 and A1016 (Table 1A).

Example 10

Separation of Mixture to Yield Pure Enantiomers A1006, A1007 and A1008 (Table 1A)

Using the same procedure as in Example 1 steps a to d; but starting with 5-methyl indan-1,3-dione in step a, and using 1-(4-morpholin-4yl-phenyl)-pyrrole-2,5-dione in step c, a mixture of compounds was obtained which was separated on preparative HPLC using a chiral column (Chiracel OD, isocratic eluent 65% $CH_3CN/H_2O$ containing 0.06% TFA; UV lamp at 205 nm; flow 7 mL/min.). The resulting three fractions were lyophilized and treated with NaOH (0.02N, 1 equiv.) to give the corresponding sodium salts as white solids.

Compound A1006 was isolated as a mixture of isomers in a 1:1 ratio.

Compounds A1007 and A1008 were each isolated as pure enantiomers.

Example 11

E2-dependent E1 DNA Binding Assay

This assay was modeled on a similar assay for SV40 T Antigen described by McKay (J. Mol. Biol., 1981, 145:471). A 400 bp radiolabeled DNA probe, containing the HPV-11 origin of replication (Chiang et al., 1992, Proc. Natl. Acad. Sci. USA 89:5799) was produced by pcr, using piasmid pBluescript™ SK encoding the origin (nucleotides 7886-61 of the HPV-11 genome in unique BAMH1 site) as template and primers flanking the origin. Radiolabel was incorporated as [$^{33}$P]dCTP. Binding assay buffer consisted of: 20 mM Tris pH 7.6, 100 mM NaCl, 1 mM DTT, 1 mM EDTA.

Other reagents used were protein A-SPA beads (type II, Amersham) and K72 rabbit polyclonal antiserum, raised against a peptide corresponding to the C-terminal 14 amino acids of HPV-11 E1. Following the protocol from Amersham, one bottle of beads was mixed with 25 mL of binding assay buffer. For the assay, a saturating amount of K72 antiserum was added to the beads and the mixture was incubated for 1 h, washed with one volume of binding assay buffer, and then resuspended in the same volume of fresh binding assay buffer. Binding reactions contained 8 ng of E2, approximately 100-200 ng of purified E1, and 0.4 ng of radiolabeled probe in a total of 80 µL of binding assay buffer. After 1 h at room temperature, 25 µL of K72 antibody-SPA bead suspension was added to with the binding reaction and mixed. After an additional hour of incubation at room temperature, the reactions were centrifuged briefly to pellet the beads and the extent of complex formation was determined by scintillation counting on a Packard TopCount™. Typically, the signal for reactions containing E1 and E2 was 20-30 fold higher than the background observed when either E1, E2, or both was omitted.

Example 12

SV40 T Antigen-DNA Binding Assay

Selectivity of the inhibitors according to the invention was assessed by activity in the E1 or E1-E2-ori binding assays and lack of activity (or lower potency) in the SV40 large T antigen assay.

This assay measures the formation of an SV40 T Antigen (TAg)-origin complex. The assay was developed by R. D. G. McKay (J. Mol. Biol. (1981) 145, 471-488). In principle, it is very similar to the E2-dependent E1-DNA binding assay (Example 12), with TAg replacing E1 and E2, and a radiolabeled SV40 ori probe replacing the HPV ori probe. The assay is used as a counterscreen for the assay of Example 13, since TAg shares functional homology to E1 and E2, but has very low sequence similarity.

The radiolabeled origin-containing DNA probe was made by PCR using pCH110 plasmid (Pharmacia) as a template. This template encodes the SV40 minimal origin of replication at nucleotides 7098-7023. Primers were "sv40-6958sens"=5'-GCC CCT AAC TCC GCC CAT CCC GC (SEQ ID NO. 1), and "sv40-206anti"=5'-ACC AGA CCG CCA CGG CTT ACG GC (SEQ ID NO. 2). The PCR product was approximately 370 base pairs long and was radiolabeled using 50 µCi/100 µL PGR reaction of dCTP ($\alpha$-$^{33}$P). Subsequent to the PCR reaction, the product was purified using either the Qiagen® PCR purification kit, or a phenol extraction/ethanol precipitation procedure. The purified product was diluted to 1.5 ng/μL (estimated by gel electrophoresis) in TE. Fresh preparations had approximately 150,000 cpm/μL.

Binding reactions were performed by mixing 30 μl of TAg solution (100 ng/well, 200 ng of a $^{33}$P-radiolabeled DNA probe, and 7.5 μl of 10×DNA binding buffer (200 mM Tris-HCl pH 7.6, 100 mM NaCl, 1 mM EDTA, 10 mM DTT) in a final volume of 75 μl. Binding reactions were allowed to proceed at room temperature for 60 min. The Large T Antigen purchased from Chimerx, at 2.0 mg/mL.

The protein-DNA complexes were immunocaptured using an α-TAg monoclonal antibody (PAb 101, subtype IgG2a, hybridoma obtained from ATCC and antibody purified in-house) bound to protein A-SPA beads. Immunoprecipitation of protein-DNA complexes was carried out for 1 hr at rt. The plates were spun briefly and the precipitated radiolabeled DNA fragments were counted on a TopCount® counter.

Example 13

Cell-based DNA Replication Assay

CHO-K1 cells were transfected using Lipofectamine Plus Reagent (Gibco/BRL) following standard procedure. Cells grown to 40-60% confluence in 100 mm tissue culture dishes were transfected simultaneously with 0.5 μg pN9-ORI (HPV-11 minimal origin of DNA replication), 0.5 μg pCR3-E1 and 0.05 μg pCR3-E2 (containing respectively HPV-11 E1 full length and HPV-11 E2 full length cloned by the TA cloning system). After 4 hours of incubation with the DNA mixture, cells were trypsinized, pooled and replated at 20,000 cells/well in a 96 well plate. Following 2 hours of attachment at 37° C., serially diluted inhibitor compounds were added for a 2 days incubation period.

The cells were washed to eliminate the compound, and the total DNA was extracted using a modified protocol of the QIAamp Blood Kit (QIAGEN). DNA was digested with Hind III (10 U/well) and Dpn1 (20 U/well) for 4 hours at 37° C. Digested DNA (10 μl) was subjected to 23 rounds of PCR amplification using the Pwo DNA polymerase Kit (Boehringer Mannheim) modified to contain 2 U of Pwo DNA polymerase, 10 μCi [α$^{33}$P]dCTP and 2 primers (each at a final concentration of 0.2 μM) per 50 μl reaction.

Cycling consisted of an initial denaturation step at 95° C. for 5 min., followed by 23 rounds of: denaturation at 94° C. for 30 sec., annealing and extension at 72° C. for 1 min. 30 sec., ending with a final extension at 72° C. for 10 min. After amplification was completed, 10 μl was analyzed on 1% agarose gel, subsequently dried at 60° C. for 1 hour, and analyzed by Phosphorimager.

To evaluate the effect of the compound on cellular DNA synthesis (and/or cellular toxicity), cell proliferation ELISA (Boehringer Mannheim), which monitor BrdU incorporation, were performed.

Example 14

Tables of Compounds

All compounds listed in Tables 1 to 10 were found to be active in the E1-E2 DNA assay presented in Example 11 with an IC$_{50}$ under 50 μM for HPV-11.

Table legend: For IC$_{50}$ A=50 μM-5 μM; B=5 μM-0.5 μM; C=<0.5 μM

Certain compounds were also tested in the SV40 TAg assay of Example 12 and were found to be inactive or less active than in the E1-E2 DNA assay, providing good evidence that these compounds are selective against the papilloma virus.

In addition, certain compounds were tested in the DNA replication cellular assay of Example 13. The results obtained indicate that they can inhibit viral replication.

TABLE 1

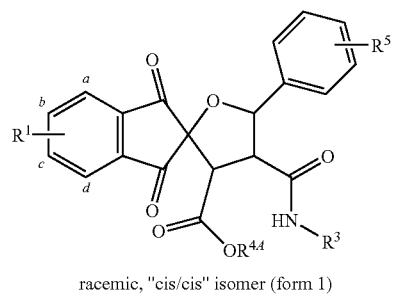

racemic, "cis/cis" isomer (form 1)

| Table 1 cpd # | R$^{44}$ | R$^1$ | ----R$^5$ | ----R$^3$ | ES MS (M + H)$^+$ *(M − H) | IC$_{50}$ (μM) |
|---|---|---|---|---|---|---|
| 1001 | Na | — | 4-Cl | (1,3-benzodioxol-5-yl) | 520 | A |
| 1002 | Na | — | 3,4-Cl | (1,3-benzodioxol-5-yl) | 552* | C |

TABLE 1-continued
racemic, "cis/cis" isomer (form 1)
| Table 1 cpd # | R^{4A} | R^1 | ----R^5 | ----R^3 | ES MS (M + H)^+ *(M − H) | IC_{50} (μM) |
|---|---|---|---|---|---|---|
| 1003 | Na | — | 4-Cl | 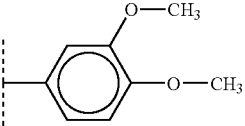 | 492* | A |
| 1004 | Na | — | 4-Cl | 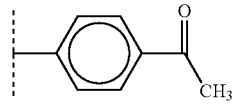 | 534* | A |
| 1005 | Na | — | 4-Cl | 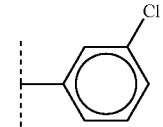 | 516* | A |
| 1006 | Na | — | 4-Cl | 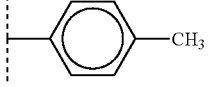 | 508* | A |
| 1007 | Na | — | 4-Cl | 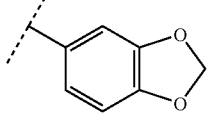 | 488* | A |
| 1008 | Na | — | 4-iPr | 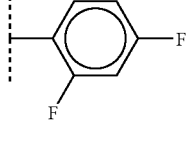 | 526* | A |
| 1009 | Na | — | 4-Cl | 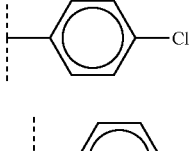 | 510* | A |
| 1010 | Na | — | 4-Cl | 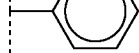 | 510* | A |
| 1011 | Na | — | 4-Cl |  | 474* | A |

TABLE 1-continued racemic, "cis/cis" isomer (form 1)

| Table 1 cpd # | R^{4A} | R^1 | ----R^5 | ----R^3 | ES MS (M + H)^+ *(M − H) | IC$_{50}$ (μM) |
|---|---|---|---|---|---|---|
| 1012 | Na | — | 4-Cl | 3-methylphenyl | 488* | A |
| 1013 | Na | — | 4-Cl | 2,3-dihydro-1H-indene | 514* | A |
| 1014 | Na | — | 4-Cl | 4-CF$_3$-phenyl | 542* | A |
| 1015 | Na | — | 3-Cl | benzo[1,3]dioxole | 518* | B |
| 1016 | Na | — | 4-CF$_3$ | benzo[1,3]dioxole | 552* | A |
| 1017 | CH$_3$ | — | 4-Cl | benzo[1,3]dioxole | 532* | A |
| 1018 | Na | — | 3-CH$_3$ | benzo[1,3]dioxole | 498* | A |
| 1019 | Na | a-F | 4-Cl | benzo[1,3]dioxole | 536* | A |

TABLE 1-continued
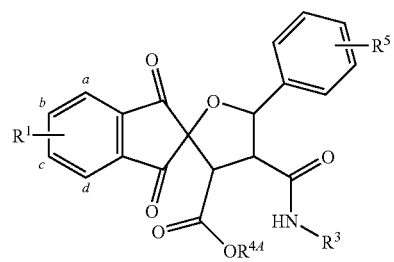
racemic, "cis/cis" isomer (form 1)
| Table 1 cpd # | $R^{4A}$ | $R^1$ | ----$R^5$ | ----$R^3$ | ES MS $(M + H)^+$ *$(M - H)$ | IC$_{50}$ ($\mu$M) |
|---|---|---|---|---|---|---|
| 1020 | Na | — | 3,5-Cl | benzo[1,3]dioxole | 552* | A |
| 1021 | Na | — | 3,4-Cl | 4-acetylphenyl | 552 | C |
| 1022 | CH$_3$ | — | 3,4-Cl | benzo[1,3]dioxole | 568 | B |
| 1023 | Na | — | 3-OCH$_3$ | benzo[1,3]dioxole | 515* | A |
| 1024 | Na | — | 3,4-CH$_3$ | benzo[1,3]dioxole | 514 | B |
| 1025 | Na | — | 3,4-Cl | 4-tert-butylphenyl | 566 | B |
| 1026 | Na | — | 3,4-F | benzo[1,3]dioxole | 556 | A |
| 1027 | Na | — | 3,4-Br | 4-acetylphenyl | 639* | C |
| 1028 | Na | — | 3,4-Cl | 4-(6-methylbenzothiazol-2-yl)phenyl | 657 | C |

TABLE 1-continued racemic, "cis/cis" isomer (form 1)

| Table 1 cpd # | R$^{4A}$ | R$^1$ | ----R$^5$ | ----R$^3$ | ES MS (M + H)$^+$ *(M − H) | IC$_{50}$ (μM) |
|---|---|---|---|---|---|---|
| 1029 | Na | — | 3-F, 4-Cl | benzo[1,3]dioxol-5-yl | 538 | B |
| 1030 | Na | — | 3-Cl, 4-F | benzo[1,3]dioxol-5-yl | 538 | B |
| 1031 | Na | — | 3-CF$_3$ | benzo[1,3]dioxol-5-yl | 554 | B |
| 1032 | Na | — | 3-Cl | 4-acetylphenyl | 518 | B |
| 1033 | Na | — | 3,4-Cl | 4-(methylthio)phenyl | 556 | B |
| 1034 | Na | — | 3,4-Cl | 4-morpholinophenyl | 595 | C |
| 1035 | Na | — | 3,4-Cl | 4-acetamidophenyl | 567 | C |
| 1036 | Na | — | 3,4-Cl | isopropyl | 476 | B |
| 1037 | Na | b-CH$_3$ | 3,4-Cl | benzo[1,3]dioxol-5-yl | 568 | B |

TABLE 1-continued racemic, "cis/cis" isomer (form 1)

| Table 1 cpd # | R$^{4A}$ | R$^1$ | ----R$^5$ | ----R$^3$ | ES MS (M + H)$^+$ *(M − H) | IC$_{50}$ (μM) |
|---|---|---|---|---|---|---|
| 1038 | Na | — | 3,4-Cl | 4-(NHC(O)OC(CH$_3$)$_3$)phenyl | 525 | B |
| 1039 | Na | — | 4-I | benzo[1,3]dioxol-5-yl | 612 | B |
| 1040 | Na | — | 3,4-Cl | isoquinolin-3-yl | 561 | B |
| 1041 | Na | d-CH$_3$ | 3,4-Cl | benzo[1,3]dioxol-5-yl | 568 | B |
| 1042 | Na | a-CH$_3$ | 3,4-Cl | benzo[1,3]dioxol-5-yl | 568 | B |
| 1043 | Na | — | 3,4-Cl | morpholin-4-yl | 519 | B |
| 1044 | Na | — | 3-Cl | 4-acetylphenyl | 519 | A |
| 1045 | Na | — | 3-F, 4-CF$_3$ | benzo[1,3]dioxol-5-yl | 572 | B |
| 1046 | Na | — | 3,4-Cl | tert-butyl | 490 | B |

TABLE 1-continued
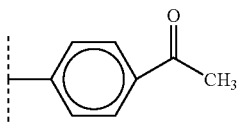
racemic, "cis/cis" isomer (form 1)
| Table 1 cpd # | R$^{4A}$ | R$^1$ | ----R$^5$ | ----R$^3$ | ES MS (M + H)$^+$ *(M − H) | IC$_{50}$ (μM) |
|---|---|---|---|---|---|---|
| 1047 | Na | — | 3,4-Cl | 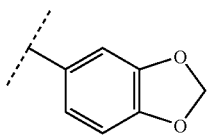 | 553 | B |
| 1048 | Na | d-F | 3,4-Cl | 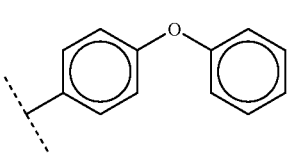 | 572 | B |
| 1049 | Na | — | 3,4-Cl | 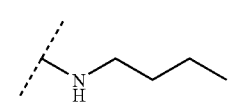 | 600* | B |
| 1050 | Na | — | 3,4-Cl | 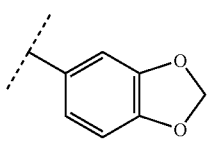 | 490 | B |
| 1051 | Na | a-F | 3,4-Cl | 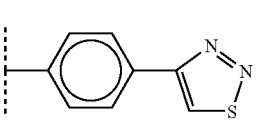 | 572 | B |
| 1052 | Na | — | 3,4-Cl | 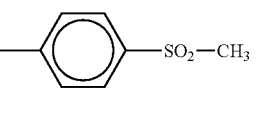 | 594 | C |
| 1053 | Na | — | 3,4-Cl | 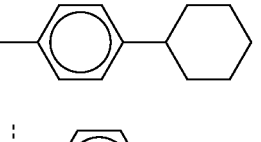 | 588 | B |
| 1054 | Na | — | 3,4-Cl | 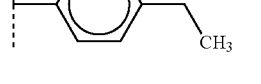 | 592 | C |
| 1055 | Na | — | 3,4-Cl | | 538 | B |

TABLE 1-continued
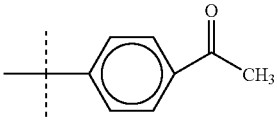
racemic, "cis/cis" isomer (form 1)
| Table 1 cpd # | R$^{4A}$ | R$^1$ | ----R$^5$ | ----R$^3$ | ES MS (M + H)$^+$ *(M − H) | IC$_{50}$ (μM) |
|---|---|---|---|---|---|---|
| 1056 | Na | — | 3,4-CH$_3$ | 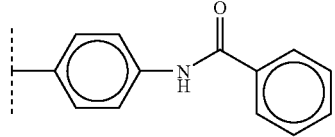 | 512 | B |
| 1057 | Na | — | 3,4-Cl |  | 629 | B |
| 1058 | Na | — | 3,4-Cl | 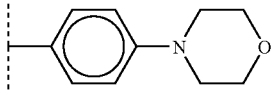 | 550 | B |
| 1059 | Na | — | 3,4-F | 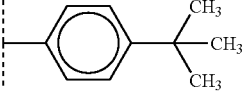 | 563 | B |
| 1060 | Na | — | 3,4-Cl | 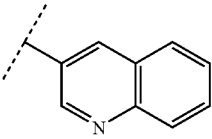 | 566 | B |
| 1061 | Na | — | 3,4-F | 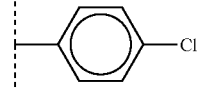 | 529 | A |
| 1062 | Na | — | 3,4-F | 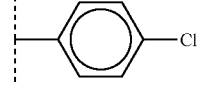 | 512 | A |
| 1063 | Na | — | 3,4-Cl | 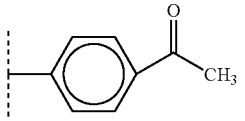 | 546 | B |
| 1064 | Na | — | 3,4-F |  | 520 | A |

TABLE 1-continued
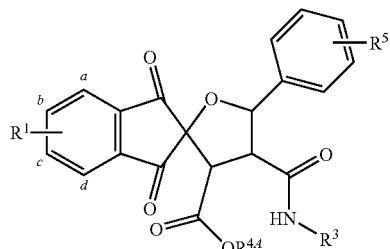
racemic, "cis/cis" isomer (form 1)
| Table 1 cpd # | R⁴·⁴ | R¹ | ----R⁵ | ----R³ | ES MS (M + H)⁺ *(M − H) | IC₅₀ (μM) |
|---|---|---|---|---|---|---|
| 1065 | Na | — | 3,4-Cl | 4-CH₃-phenyl | 524 | B |
| 1066 | Na | — | 3,4-Cl | 2-phenylcyclopropyl | 550 | C |
| 1067 | Na | — | 3-F,4-CF₃ | 4-acetylphenyl | 570 | A |
| 1068 | Na | — | 3,4-F | phenyl | 478 | A |
| 1069 | Na | b-Br | 3,4-Cl | 4-acetylphenyl | 629 | A |
| 1070 | Na | — | 3,4-Cl | 4-cyanophenyl | 534* | B |
| 1071 | Na | — | 3,4-CH₃ | quinolin-3-yl | 519* | A |
| 1072 | Na | — | 3,4-Br | 4-CH₃-phenyl | 611 | C |
| 1073 | Na | — | 3,4-F | 4-(SCH₃)-phenyl | 524 | A |
| 1074 | Na | — | 3,4-Br | phenyl | 599 | C |

TABLE 1-continued
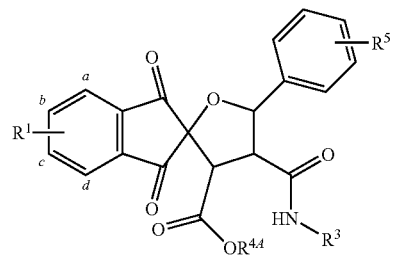
racemic, "cis/cis" isomer (form 1)
| Table 1 cpd # | $R^{4A}$ | $R^1$ | ----$R^5$ | ----$R^3$ | ES MS $(M + H)^+$ *$(M - H)$ | $IC_{50}$ (μM) |
|---|---|---|---|---|---|---|
| 1075 | Na | — | 3,4-Br | morpholine-N-yl | 606* | B |
| 1076 | Na | — | 3,4-Br | 4-(1,2,3-thiadiazol-4-yl)phenyl | 681 | C |
| 1077 | Na | — | 3,4-Cl | 2-phenylethyl | 537* | C |
| 1078 | Na | — | 3,4-Br | 4-morpholinophenyl | 684 | C |
| 1079 | Na | — | 3,4-Br | 4-isopropylphenyl | 673 (M + 18) | A |
| 1080 | Na | — | 3-CN | 1,3-benzodioxol-5-yl | 511 | A |
| 1081 | Na | — | 3,4-Br | 4-(methylthio)phenyl | 646 | C |
| 1082 | Na | — | 3,4-Cl | cyclohexyl | 516 | B |
| 1083 | Na | — | 3,4-F | 4-(1,2,3-thiadiazol-4-yl)phenyl | 562 | B |
| 1084 | Na | — | 3,4-Br | 1,3-benzodioxol-5-ylmethyl | 644 | C |

TABLE 1-continued
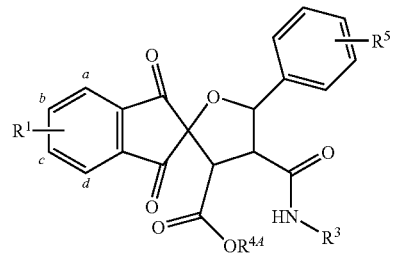
racemic, "cis/cis" isomer (form 1)
| Table 1 cpd # | R[4A] | R[1] | ----R[5] | ----R[3] | ES MS (M + H)+ *(M − H) | IC$_{50}$ (μM) |
|---|---|---|---|---|---|---|
| 1085 | Na | — | 3-CN | 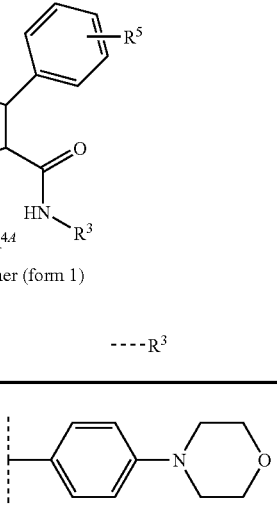 | 552 | A |
| 1086 | Na | — | 3,4-Br | 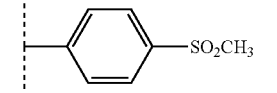 | 676 | C |
| 1087 | Na | — | 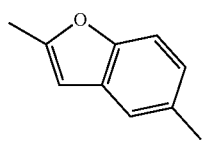 | 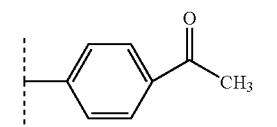 | 558 | A |
| 1088 | Na | — | 3,4-Br | 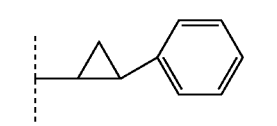<br>stereochemistry undetermined | 639 | B |
| 1089 | Na | — | 3,4-Br | 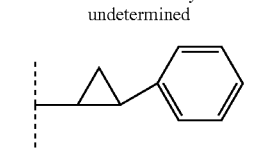<br>stereochemistry undetermined | 639 | C |
| 1090 | Na | 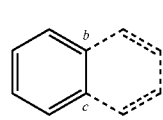 | 3,4-Cl |  | 602 | A |
| 1091 | Na | 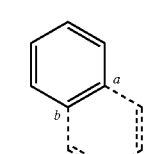 | 3,4-Cl | 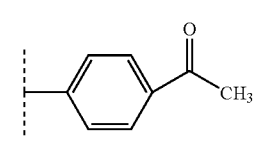 | 602 | A |
| 1092 | Na | — | 3,4-Br | 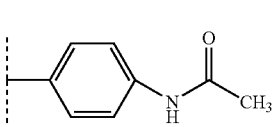 | 654.8* | C |
| 1093 | Na | — | 3-Cl, 4-F | 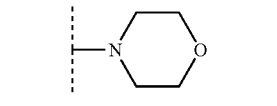 | 503 | A |

TABLE 1-continued
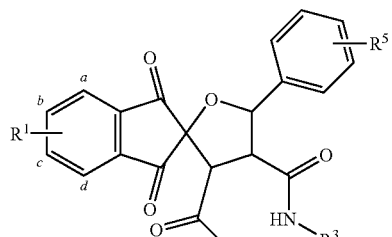
racemic, "cis/cis" isomer (form 1)
| Table 1 cpd # | R⁴ᴬ | R¹ | ----R⁵ | ----R³ | ES MS (M + H)⁺ *(M − H) | IC₅₀ (μM) |
|---|---|---|---|---|---|---|
| 1094 | Na | — | 3-Cl, 4-F | 4-acetylphenyl | 536 | B |
| 1095 | Na | naphthyl (c,d fused) | 3,4-Cl | 4-acetylphenyl | 602 | A |
| 1096 | Na | — | 3,4-Cl | 3,5-difluorophenyl | 546 | B |
| 1097 | Na | — | 3,4-Br | 2-phenylethyl | 627.9 | C |
| 1098 | Na | — | 3,4-Cl | indan-2-yl | 550 | B |
| 1099 | Na | — | 3,4-Br | cyclohexylmethyl | 606 | C |
| 1100 | Na | — | 3,4-Cl | 3-benzoylphenyl | 614 | B |
| 1101 | Na | — | 3,4-Cl | 4-chlorobenzyl | 544 | B |

TABLE 1-continued
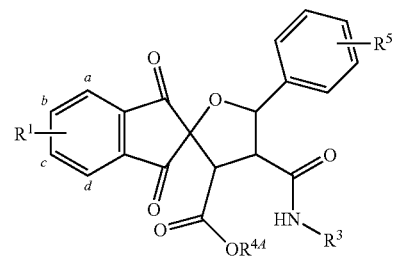
racemic, "cis/cis" isomer (form 1)
| Table 1 cpd # | $R^{4A}$ | $R^1$ | ----$R^5$ | ----$R^3$ | ES MS $(M + H)^+$ *$(M - H)$ | $IC_{50}$ (μM) |
|---|---|---|---|---|---|---|
| 1102 | Na | — | 3,4-Br | 3-Cl,4-Br-phenyl | 709 | B |
| 1103 | Na | — | 3,4-Br | 3-benzoylphenyl | 701.9 | B |
| 1104 | Na | — | 3,4-Cl | 3-Cl,4-Br-phenyl | 623.9 | B |
| 1105 | Na | — | 3,4-Br | 3,4-F-phenyl | 635.9 | B |
| 1106 | Na | b-F | 3,4-Cl | 4-acetylphenyl | 570 | B |
| 1107 | Na | c-F | 3,4-Cl | 4-acetylphenyl | 570 | B |
| 1108 | Na | — | 3,4-Cl | 4-acetamidophenyl | 565* | B |
| 1109 | Na | — | 3,4-Br | 3,5-F-phenyl | 336 | B |

TABLE 1-continued
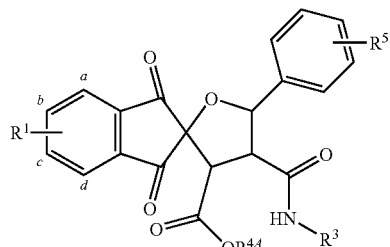
racemic, "cis/cis" isomer (form 1)
| Table 1 cpd # | R4A | R1 | ----R5 | ----R3 | ES MS (M + H)+ *(M − H) | IC50 (μM) |
|---|---|---|---|---|---|---|
| 1110 | Na | — | 3,4-Br | 4-Cl-phenyl | 634 | C |
| 1111 | Na | — | 3,4-Cl | 3,4-F-phenyl | 546 | B |
| 1112 | Na | — | 3,4-Cl | 4-OCF3-phenyl | 594 | B |
| 1113 | Na | — | 3,4-Br | 2-indanyl | 638* | C |
| 1114 | Na | c-Cl | 3,4-Cl | 4-acetylphenyl | 586 | B |
| 1115 | Na | — | 3-Cl, 4-F | 2-phenylethyl | 522 | B |
| 1116 | Na | b-Cl | 3,4-Cl | 4-acetylphenyl | 586 | A |
| 1117 | Na | — | 3,4-Cl | 6-nitro-1,3-benzodioxol-5-yl | 599 | B |
| 1118 | Na | — | 3,4-Br | 4-OCF3-phenyl | 684 | B |

TABLE 1-continued
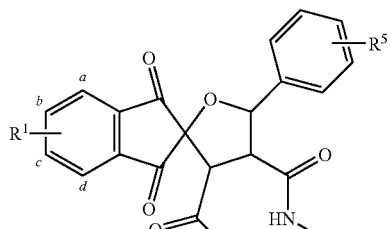
racemic, "cis/cis" isomer (form 1)
| Table 1 cpd # | $R^{4.4}$ | $R^1$ | ----$R^5$ | ----$R^3$ | ES MS $(M + H)^+$ *$(M - H)$ | $IC_{50}$ (µM) |
|---|---|---|---|---|---|---|
| 1119 | Na | — | 3,4-Br | 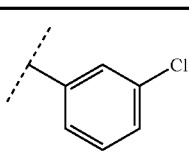 | 634 | C |
| 1120 | Na | — | 3-Cl, 4-F | 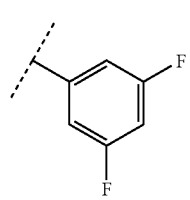 | 530 | B |
| 1121 | Na | — | 3-Cl, 4-F | 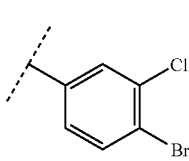 | 608 | B |
| 1122 | Na | — | 3-Cl, 4-F | 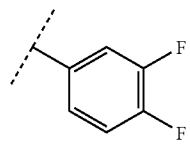 | 530 | A |
| 1123 | Na | — | 3,4-Cl | 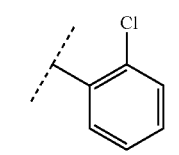 | 544 | C |
| 1124 | Na | — | 3,4-Cl | 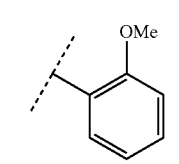 | 540 | B |
| 1125 | Na | — | 3,4-Cl | 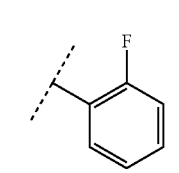 | 528 | C |

TABLE 1-continued
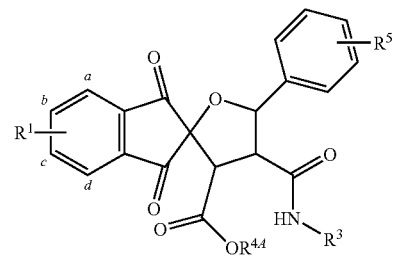
racemic, "cis/cis" isomer (form 1)
| Table 1 cpd # | R⁴·⁴ | R¹ | ----R⁵ | ----R³ | ES MS (M + H)⁺ *(M − H) | IC₅₀ (µM) |
|---|---|---|---|---|---|---|
| 1126 | Na | — | 3,4-Cl | 3,5-dimethylphenyl | 538 | B |
| 1127 | Na | — | 3,4-Cl | 3-cyanophenyl | 535 | B |
| 1128 | Na | — | 3,4-Cl | 4-morpholinophenyl | 590 | B |
| 1129 | Na | c-OMe | 3,4-Cl | 4-acetylphenyl | 581.9 | A |
| 1130 | Na | b-OMe | 3,4-Cl | 4-acetylphenyl | 579.9* | A |
| 1131 | Na | — | 3-Cl, 4-F | 4-OCF₃-phenyl | 578 | B |
| 1132 | Na | — | 3,4-F | 4-methylphenyl | 492 | A |
| 1133 | Na | — | 3,4-Cl | 2,3-dimethylphenyl | 536* | B |
| 1134 | Na | — | 3,4-Br | 3,4-dichlorophenyl | 665.6* | C |

TABLE 1-continued
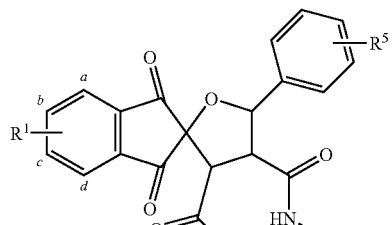
racemic, "cis/cis" isomer (form 1)
| Table 1 cpd # | $R^{4A}$ | $R^1$ | ----$R^5$ | ----$R^3$ | ES MS $(M + H)^+$ *$(M - H)$ | $IC_{50}$ ($\mu M$) |
|---|---|---|---|---|---|---|
| 1135 | Na | — | 3,4-Cl | 2-Cl-phenylpropyl | 570* | C |
| 1136 | Na | — | 3,4-Cl | 2-(ethoxy)phenylmethyl | 554 | A |
| 1137 | Na | — | 3,4-Cl | 2,5-dimethoxyphenylpropyl | 598 | B |
| 1138 | Na | — | 3,4-Cl | 2-thienylpropyl | 544 | C |
| 1139 | Na | — | 3,4-Cl | 2-(trifluoromethoxy)phenylmethyl | 594 | B |

TABLE 1-continued
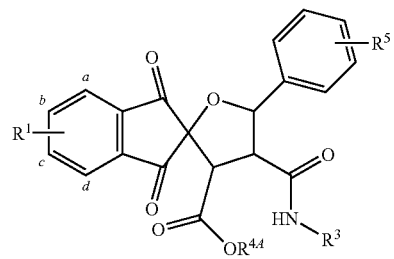
racemic, "cis/cis" isomer (form 1)
| Table 1 cpd # | R⁴·⁴ | R¹ | ----R⁵ | ----R³ | ES MS (M + H)⁺ *(M − H) | IC₅₀ (μM) |
|---|---|---|---|---|---|---|
| 1140 | Na | — | 3,4-Cl |  | 830 | B |
| 1141 | Na | — | 3-NHC(O)(CH₂)₃CH₃, 4-Cl |  | 617 | B |
| 1142 | Na | — | 3,5-Cl | 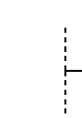 | 590 | C |
| 1143 | Na | b-F | 3,4-Br |  | 702.9 | C |
| 1144 | Na | c-F | 3,4-Br |  | 702.9 | C |

TABLE 1A

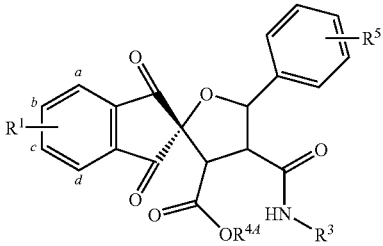

enantiomerically pure, "cis/cis" isomer (form 1)

| Table 1A cpd # | R$^{4A}$ | R$^1$ | —R$^5$ | —R$^3$ | ES MS (M + H)$^+$ *(M − H) | IC$_{50}$ (μM) |
|---|---|---|---|---|---|---|
| A1001 | Na | — | 3,4-Br | 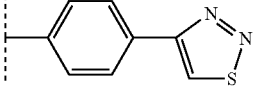<br>stereochemistry undetermined | 683.8 | A |
| A1002 | Na | — | 3,4-Br | 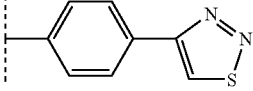<br>stereochemistry undetermined | 683.8 | C |
| A1003 | Na | mixture b-Me & c-Me | 3,4-Cl | 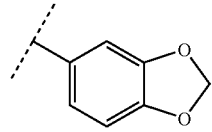<br>stereochemistry undetermined | 568 | A |
| A1004 | Na | b-Me | 3,4-Cl | 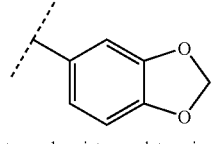<br>stereochemistry undetermined | 568 | A |
| A1005 | Na | c-Me | 3,4-Cl | 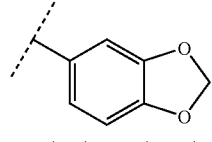<br>stereochemistry undetermined | 568 | C |
| A1006 | Na | mixture b-Me & c-Me | 3,4-Cl | 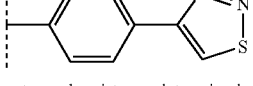<br>stereochemistry undetermined | 608 | A |
| A1007 | Na | b-Me | 3,4-Cl | 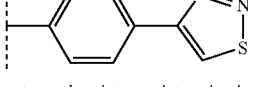<br>stereochemistry undetermined | 608 | B |
| A1008 | Na | c-Me | 3,4-Cl | 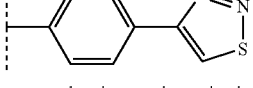<br>stereochemistry undetermined | 608 | C |

TABLE 1A-continued

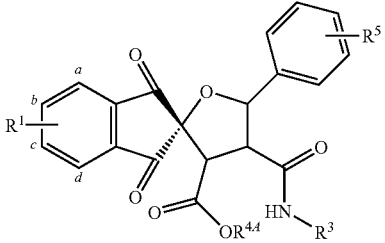

enantiomerically pure, "cis/cis" isomer (form 1)

| Table 1A cpd # | R$^{4A}$ | R$^1$ | —R$^5$ | —R$^3$ | ES MS (M + H)$^+$ *(M − H) | IC$_{50}$ (μM) |
|---|---|---|---|---|---|---|
| A1009 | Na | mixture b-Me & c-Me | 3,4-Br | 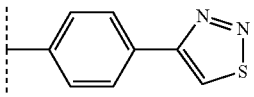<br>stereochemistry undetermined | 697.9 | A |
| A1010 | Na | b-Me | 3,4-Br | 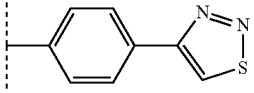<br>stereochemistry undetermined | 697.9 | B |
| A1011 | Na | c-Me | 3,4-Br | 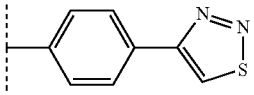<br>stereochemistry undetermined | 697.9 | C |
| A1012 | Na | — | 3,4-Br | 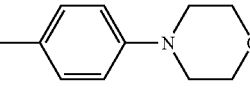<br>stereochemistry undetermined | 683* | A |
| A1013 | Na | — | 3,4-Br | 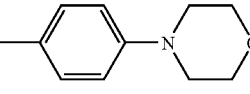<br>stereochemistry undetermined | 683* | C |
| A1014 | Na | c-Me | 3,4-Br | 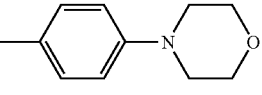 | 699 | C |
| A1015 | Na | b-F, c-Me | 3,4-Br | 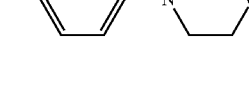 | 716.8 | C |
| A1016 | Na | b-Me, c-F | 3,4-Br | 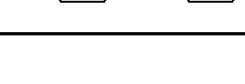 | 717 | B |

TABLE 1B enantiomerically pure, "cis/cis" isomer (form 3)

| Table 1B cpd # | $R^1$ | $R^5$ | $R^3$ | ES MS $(M + H)^+$ *$(M - H)$ | $IC_{50}$ ($\mu$M) |
|---|---|---|---|---|---|
| B1001 | b-Me, c-Me (mixture) | 3,4-Br | 4-morpholinophenyl | 699 | A |
| B1002 | b-Me | 3,4-Br | 4-morpholinophenyl | 699 | C |
| B1003 | c-Me | 3,4-Br | 4-morpholinophenyl | 699 | C |
| B1004 | b-Me | 3,4-Br | 2-(2-chlorophenyl)ethyl | 676 | A |
| B1005 | c-Me | 3,4-Br | 2-(2-chlorophenyl)ethyl | 676 | A |
| B1006 | b-Me | 3,4-Br | 2-(2-chlorophenyl)ethyl | 676 | B |
| B1007 | c-Me | 3,4-Br | 2-(2-chlorophenyl)ethyl | 676 | C |
| B1008 | b-F, c-Me | 3,4-Br | 4-morpholinophenyl | 716.6 | C |

TABLE 1C

| Table 1C cpd # | R⁵ | R³ | ES MS (M + H)⁺ *(M − H) | IC₅₀ (μM) |
|---|---|---|---|---|
| C1001 | 3,4-Cl | 4-acetylphenyl | 572 | A |
| C1002 | 3,4-Br | 4-(morpholin-4-yl)phenyl | 704 | B |
| C1003 | 3,4-Br | 4-((tert-butoxycarbonylamino)methyl)phenyl | 747 | B |

TABLE 1D enantiomerically pure "cis/cis" isomer (form 3)

| Table 1D cpd # | R⁵ | R³ | ES MS (M + H⁺ *(M − H) | IC₅₀ (μM) |
|---|---|---|---|---|
| D1001 | 3,4-Cl | 4-acetylphenyl | 572 | C |
| D1002 | 3,4-Br | 4-(morpholin-4-yl)phenyl | 704 | C |
| D1003 | 3,4-Br | 4-((tert-butoxycarbonylamino)methyl)phenyl | 747 | C |

TABLE 1D-continued enantiomerically pure "cis/cis" isomer (form 3)

| Table 1D cpd # | R⁵ | R³ | ES MS (M + H⁺ *(M − H) | IC$_{50}$ (μM) |
|---|---|---|---|---|
| D1004 | 3,4-Br | (4-methylbenzyl)acetamide group | 691 | C |

TABLE 2 racemic, "cis/cis" isomer (form 2)

| Table 2 cpd # | —R⁵ | —R³ | ES MS (M + H)⁺ *(M − H) | IC$_{50}$ (μM) |
|---|---|---|---|---|
| 2001 | 4-Cl | benzo[1,3]dioxol-5-ylmethyl | 500* | A |
| 2002 | 4-Cl | 3,4-dimethoxyphenyl | 516* | A |
| 2003 | 4-Cl | 4-acetylphenyl | 498* | A |
| 2004 | 4-Cl | 4-fluorophenyl | 474* | A |

TABLE 2-continued
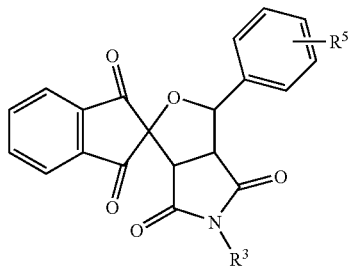
racemic, "cis/cis" isomer (form 2)
| Table 2 cpd # | —R$^5$ | —R$^3$ | ES MS (M + H)$^+$ *(M − H) | IC$_{50}$ (μM) |
|---|---|---|---|---|
| 2005 | 3-Cl | benzo[1,3]dioxol-5-yl | 500* | B |
| 2006 | 4-Cl | 4-methylphenyl | 470* | A |
| 2007 | 4-Cl | 4-chlorophenyl | 490* | A |
| 2008 | 4-CF$_3$ | benzo[1,3]dioxol-5-yl | 534* | A |
| 2009 | 4-Cl | 3-chlorophenyl | 490* | A |
| 2010 | 4-Cl | 3-methylphenyl | 470* | A |
| 2011 | 4-Cl | 3-trifluoromethylphenyl | 524* | A |
| 2012 | 4-Cl | 2,3-dihydro-1H-inden-5-yl | 496* | A |
| 2013 | 3,4-Cl | benzo[1,3]dioxol-5-yl | 534* | B |

TABLE 2-continued
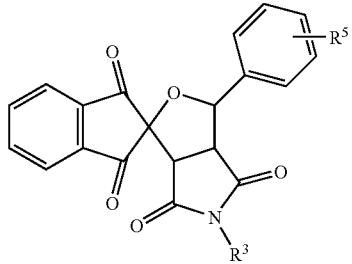
racemic, "cis/cis" isomer (form 2)
| Table 2 cpd # | —R⁵ | —R³ | ES MS $(M + H)^+$ *(M − H) | IC$_{50}$ (μM) |
|---|---|---|---|---|
| 2014 | 3-CH₃ | 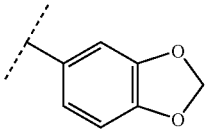 | 480* | A |
| 2015 | 4-Cl | 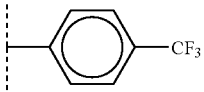 | 524* | A |
| 2016 | 3,4-Cl | 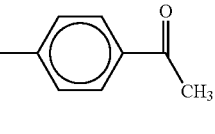 | 552 (M + 18) | B |
| 2017 | 4-I | 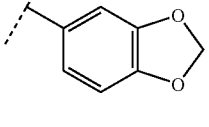 | 612 (M + 18) | A |
| 2018 | 3,4-Cl | 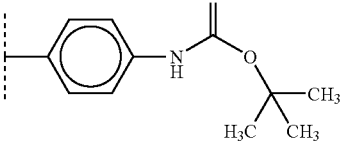 | 624 (M + 18) | A |
| 2019 | 3,4-Cl | 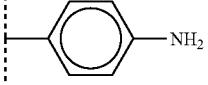 | 524 (M + 18) | B |
| 2020 | 4-OH, 5-Cl | 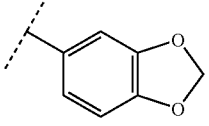 | 534 (M + 18) | B |
| 2021 | 3,4-Cl |  | 526 (M + 18) | C |

TABLE 2-continued racemic, "cis/cis" isomer (form 2)

| Table 2 cpd # | —R[5] | —R[3] | ES MS (M + H)+ *(M − H) | IC$_{50}$ (μM) |
|---|---|---|---|---|
| 2022 | 3,4-Cl | 4-benzyl-NH-CH2-C(O)-NH-CH2CH2-NH-naphthyl-5-SO2 | 827 | A |
| 2023 | 3,4-Br | 4-morpholinophenyl | 667 | C |

TABLE 3 racemic, "cis/cis" isomer (form 3)

| Table 3 cpd # | R[1] | —Y | —R[3] | ES MS (M + H)+ *(M − H) | IC$_{50}$ (μM) |
|---|---|---|---|---|---|
| 3001 | — | 3,5-diCl-phenyl | benzo[1,3]dioxol-5-yl | 552* | B |
| 3002 | — | 4-Cl-phenyl | cyclohexyl | 482 | A |
| 3003 | — | 4-Cl-phenyl | benzyl | 488* | A |

TABLE 3-continued
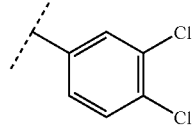
racemic, "cis/cis" isomer (form 3)
| Table 3 cpd # | R¹ | —Y | —R³ | ES MS (M + H)⁺ *(M − H) | IC$_{50}$ (μM) |
|---|---|---|---|---|---|
| 3004 | — | 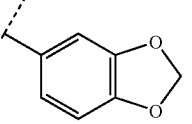 | 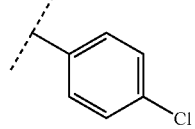 | 566* | A |
| 3005 | — | 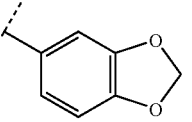 | 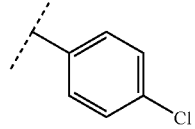 | 518* | A |
| 3006 | — | 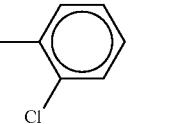 | 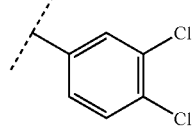 | 510 | A |
| 3007 | — | 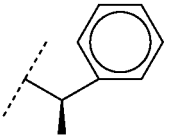 | 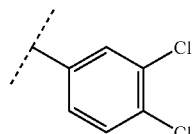 | 538 | A |
| 3008 | — | 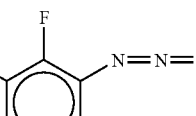 | 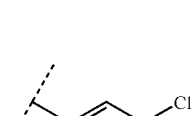 | 637 | A |
| 3009 | — | 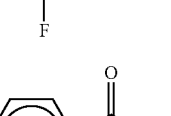 | 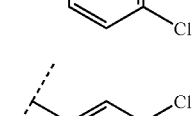 | 552 | C |
| 3100 | — |  | 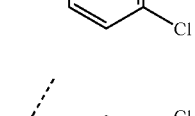 | 540 | A |
| 3011 | — | 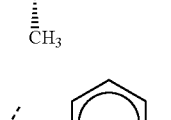 | | 526 | B |

TABLE 3-continued racemic, "cis/cis" isomer (form 3)

| Table 3 cpd # | R¹ | —Y | —R³ | ES MS (M + H)⁺ *(M − H) | IC$_{50}$ (μM) |
|---|---|---|---|---|---|
| 3012 | — | 3-chloro-1H-indol-2-yl | 4-acetylphenyl | 569* | B |
| 3013 | c-Me | 3,4-dibromophenyl | 4-(1,2,3-thiadiazol-4-yl)phenyl | 697 | C |
| 3014 | — | 3,4-dichlorophenyl | 2-(pyridin-3-yl)ethyl | 588 | B |
| 3015 | — | 3,4-dichlorophenyl | 2-(pyridin-4-yl)ethyl | 544 | B |
| 3016 | b-F | 3,4-dibromophenyl | 4-morpholinophenyl | 702 | C |
| 3017 | c-F | 3,4-dibromophenyl | 4-morpholinophenyl | 702 | C |

TABLE 4 racemic, "cis/cis" isomer (form 1)

| Table 4 cpd # | —Y | —R³ | ES MS (M + H)⁺ *(M − H) | IC$_{50}$ (μM) |
|---|---|---|---|---|
| 4001 | 2-naphthyl | benzo[1,3]dioxol-5-yl | 536 | B |
| 4002 | benzofuran-2-yl | benzo[1,3]dioxol-5-yl | 526 | A |
| 4003 | benzo[1,3]dioxol-5-yl | benzo[1,3]dioxol-5-yl | 530 | A |
| 4004 | 2-naphthyl | 4-acetylphenyl | 534 | B |
| 4005 | styryl | 4-acetylphenyl | 510 | A |
| 4006 | 3-bromostyryl | 4-acetylphenyl | 588 | A |

TABLE 4-continued racemic, "cis/cis" isomer (form 1)

| Table 4 cpd # | —Y | —R³ | ES MS (M + H)⁺ *(M − H) | IC$_{50}$ (μM) |
|---|---|---|---|---|
| 4007 | 2-bromostyryl | 4-acetylphenyl | 588 | B |
| 4008 | α-methylstyryl | 4-acetylphenyl | 523 | A |
| 4009 | β-methylstyryl | 4-acetylphenyl | 523 | A |
| 4010 | 2,3-dichlorostyryl | 4-acetylphenyl | 576* | B |
| 4011 | 2-methylstyryl | 4-acetylphenyl | 522* | A |
| 4012 | α-bromostyryl | 4-acetylphenyl | 589 | A |

TABLE 5

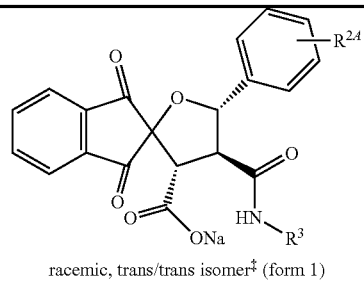

racemic, trans/trans isomer‡ (form 1)

| Table 5 cpd # | —R⁵ | —R³ | ES MS (M + H) | IC₅₀ (μM) |
|---|---|---|---|---|
| 5001 | 3,4-Cl | 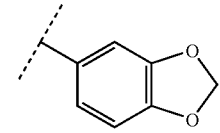 | 554 | B |

‡relative stereochemistry shown

TABLE 6

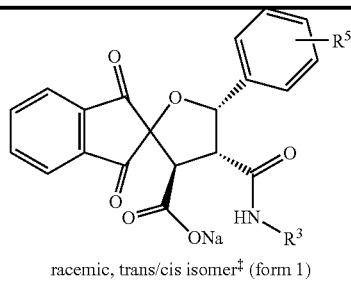

racemic, trans/cis isomer‡ (form 1)

| Table 6 cpd # | —R⁵ | —R³ | ES MS (M + H)⁺ | IC₅₀ (μM) |
|---|---|---|---|---|
| 6001 | 3,4-Cl | 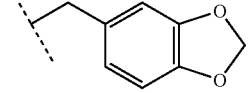 | 568 | A |

‡relative stereochemistry shown

TABLE 7

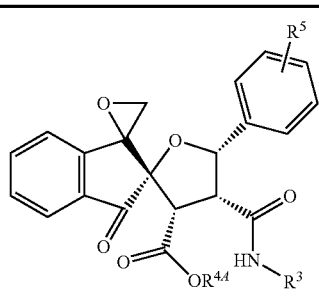

racemic, "cis/cis" isomer‡ (form 1)

| Table 7 cpd # | R⁴ᴬ | —R⁵ | —R³ | ES MS (M + H)⁺ | IC₅₀ (μM) |
|---|---|---|---|---|---|
| 7001 | OCH₃ | 3,4-Cl | 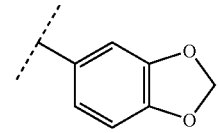 | 582 | A |

‡relative stereochemistry shown

TABLE 8

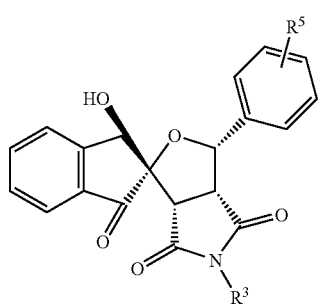

racemic, "cis/cis" isomer‡ (form 2)

| Table 8 cpd # | —R⁵ | —R³ | ES MS (M + H)⁺ | IC₅₀ (μM) |
|---|---|---|---|---|
| 8001 | 3,4-Cl | 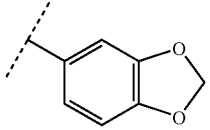 | 556 | B |

‡relative stereochemistry shown

TABLE 9

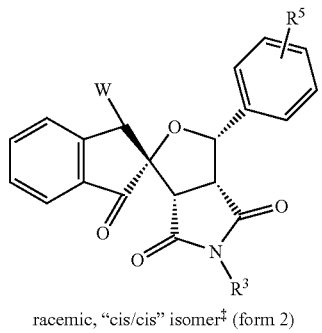

racemic, "cis/cis" isomer‡ (form 2)

| Table 9 cpd # | W | —R⁵ | —R³ | ES MS (M + H)⁺ | IC₅₀ (μM) |
|---|---|---|---|---|---|
| 9001 | 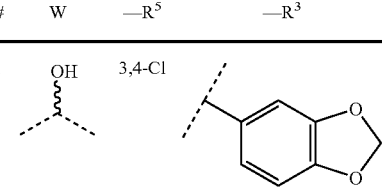 OH | 3,4-Cl | | 540 | A |

‡relative stereochemistry shown

TABLE 10

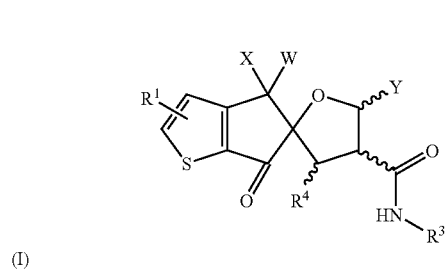

racemic, cis/trans isomer‡ (form 1)

| Table 10 Cpd # | —Y | —R³ | ES MS (M + H)⁺ | IC$_{50}$ (μM) |
|---|---|---|---|---|
| 10,001 | 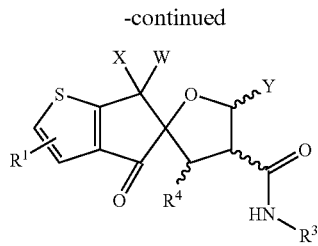 | | 683 | B |

‡relative stereochemistry shown

---

---

We claim:

1. A compound of formula (I″) or formula (I‴) or an enantiomer or diastereoisomer thereof:

wherein:
X is H and W is OH; or X and W together form a carbonyl group or an epoxide group;
R¹ is H; or one or two substituents independently selected from the group consisting of: hydroxy; halo; lower alkyl;

lower alkoxy; lower thioalkyl; haloalkyl; or —C(O)R² wherein R² is lower alkyl, aryloxy or benzyloxy;

Y is phenyl optionally mono- or di-substituted with R⁵ or C(O)R⁶, wherein R⁵ is lower alkyl, lower cycloalkyl, lower alkoxy, halo, hydroxy, nitrile or trifluoromethyl, and R⁶ is lower alkyl, lower cycloalkyl, lower alkoxy, hydroxy or trifluoromethyl; said phenyl ring being optionally fused with a saturated or unsaturated 4 to 6-membered carbocyclic ring;

or Y is ethylene-phenyl, said ethylene moiety being optionally mono-substituted with lower alkyl wherein said phenyl ring is optionally mono- or di-substituted with R⁵ or C(O)R⁶, wherein R⁵ and R⁶ are as defined above; said phenyl ring being optionally fused with a saturated or unsaturated 4 to 6-membered carbocyclic ring;

R³ is selected from the group consisting of: lower alkyl, lower cycloalkyl, aryl or lower aralkyl, all of which are optionally mono- or di-substituted with:

lower alkyl, lower cycloalkyl, haloalkyl, halo, CN, azido, lower alkoxy, (lower alkyl)acyl, $C_{1-6}$ thioalkyl, $C_{1-6}$ alkylsulfonyl, NHC(O)-lower alkyl, NHC(O)-aryl, NHC(O)—O-lower alkyl or, NHC(O)O-aryl; aryl or aryloxy, hydroxy, nitro, amino or Het, said Het being optionally mono- or di-substituted with lower alkyl lower cycloalkyl, lower alkoxy, halo, hydroxy, nitrile trifluoromethyl, or C(O)R⁶ wherein R⁶ is as defined above;

provided that when R³ is aryl mono- or disubstituted with Het, Het is not optionally substituted morpholine or an optionally substituted five-membered, unsaturated heterocycle containing from one to three heteroatoms selected from nitrogen, oxygen and sulfur;

said lower cycloalkyl, aryl, lower aralkyl or Het being optionally fused with a saturated or unsaturated 4 to 6-membered ring optionally containing a heteroatom selected from N, 0 and S; and R⁴ is a carboxylic acid, a salt or an ester thereof.

2. A compound according to claim 1, selected from the compounds of formula (Ia) to (Ih):

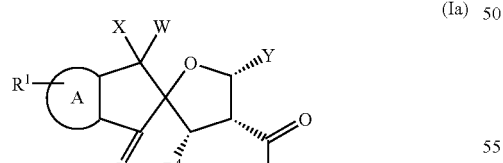
(Ia)

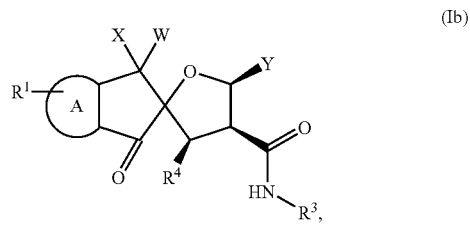
(Ib)

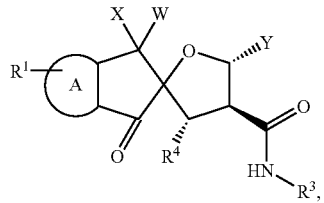
(Ic)

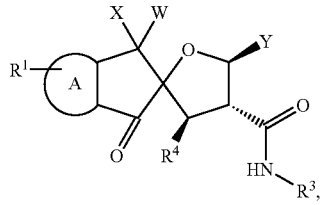
(Id)

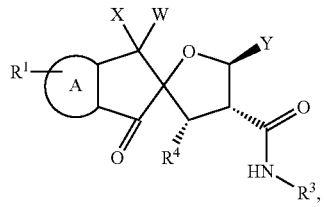
(Ie)

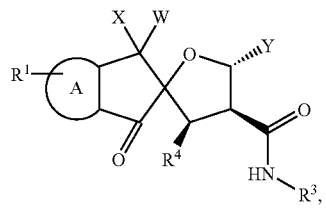
(If)

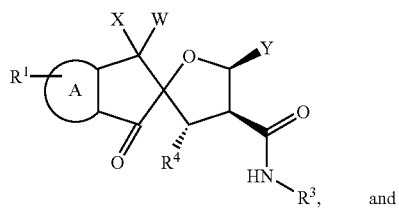
(Ig) and

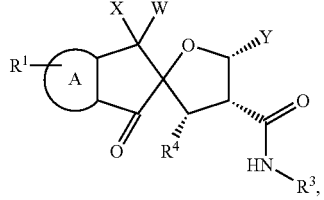
(Ih)

wherein X, W, R¹, Y, R³, and R⁴ are as defined in claim 1 and A is a thienyl ring as shown for formula (I″) or (I‴).

3. A composition comprising a mixture of a compound of formula (Ia) and a compound of formula (Ib), each according to claim 2.

4. A composition comprising a mixture of a compound of formula (Ic) and a compound of formula (Id), each according to claim 2.

5. A composition according to claim 3, wherein said mixture is racemic.

6. A composition according to claim 4, wherein said mixture is racemic.

7. A compound of formula (Ia) according to claim 2, as a pure enantiomer.

8. A compound of formula (Ib) according to claim 2, as a pure enantiomer.

9. A compound of formula (Ic) according to claim 2, as a pure enantiomer.

10. A compound of formula (Id) according to claim 2, as a pure enantiomer.

11. A compound of claim 1, wherein X is H and W is OH; or X and W together form a carbonyl group.

12. A compound of claim 1, wherein X is H and W is OH.

13. A compound according to claim 1, wherein $R^1$ is H, halo or $C_{1-4}$ alkyl.

14. A compound according to claim 1, wherein $R^1$ is H, fluoro or methyl.

15. A compound according to claim 1, wherein $R^1$ is H or methyl.

16. A compound according to claim 1, wherein Y is phenyl optionally mono- or di-substituted with $R^5$ or $C(O)R^6$, wherein $R^5$ is lower alkyl, lower cycloalkyl, lower alkoxy, halo, hydroxy, nitrile or trifluoromethyl, and $R^6$ is lower alkyl, lower cycloalkyl, lower alkoxy, hydroxy or trifluoromethyl; said phenyl ring being optionally fused with a saturated or unsaturated 4 to 6-membered carbocyclic ring.

17. A compound according to claim 1, wherein Y is naphthyl, CH=CH— phenyl, C(CH$_3$)=CH-phenyl or phenyl, wherein the phenyl ring is optionally mono- or di-substituted at the 3, 4, or 5 position with $R^5$, wherein $R^5$ is halo, $C_{1-4}$ alkyl hydroxy or $CF_3$.

18. A compound according to claim 1, wherein Y is naphthyl or phenyl, wherein the phenyl ring is optionally mono- or di-substituted at the 3, 4, or 5 position with $R^5$, wherein $R^5$ is halo, $C_{1-4}$ alkyl, hydroxy or $CF_3$.

19. A compound according to claim 1, wherein Y is phenyl optionally substituted with: 3,4-Cl; 3-F,4-Cl; 3-Cl,4-F; 3,4-Br; 3-F,4-CH$_3$; 3,4-CH$_3$; or 3-CF$_3$.

20. A compound according to claim 1, wherein Y is phenyl optionally substituted with: 3,4-Cl and 3,4-Br.

21. A compound according to claim 1, wherein $R^3$ is selected from the group consisting of:

cyclohexyl; $C_{1-6}$ alkyl; ($C_{1-6}$ alkyl)phenyl wherein the phenyl ring is optionally substituted with:
lower alkyl, CF$_3$, halo, CN, azido, lower alkoxy, (lower alkyl)acyl, $C_{1-6}$ thioalkyl, $C_{1-6}$ alkylsulfonyl, NHC(O)-lower alkyl, aryl, aryloxy, hydroxy, nitro, or amino or Het, said Het optionally mono- or di-substituted with lower alkyl lower alkoxy, halo, hydroxy, nitrile or trifluoromethyl.

22. A compound according to claim 1, wherein $R^3$ is selected from the group consisting of:

$C_{1-6}$ alkyl;

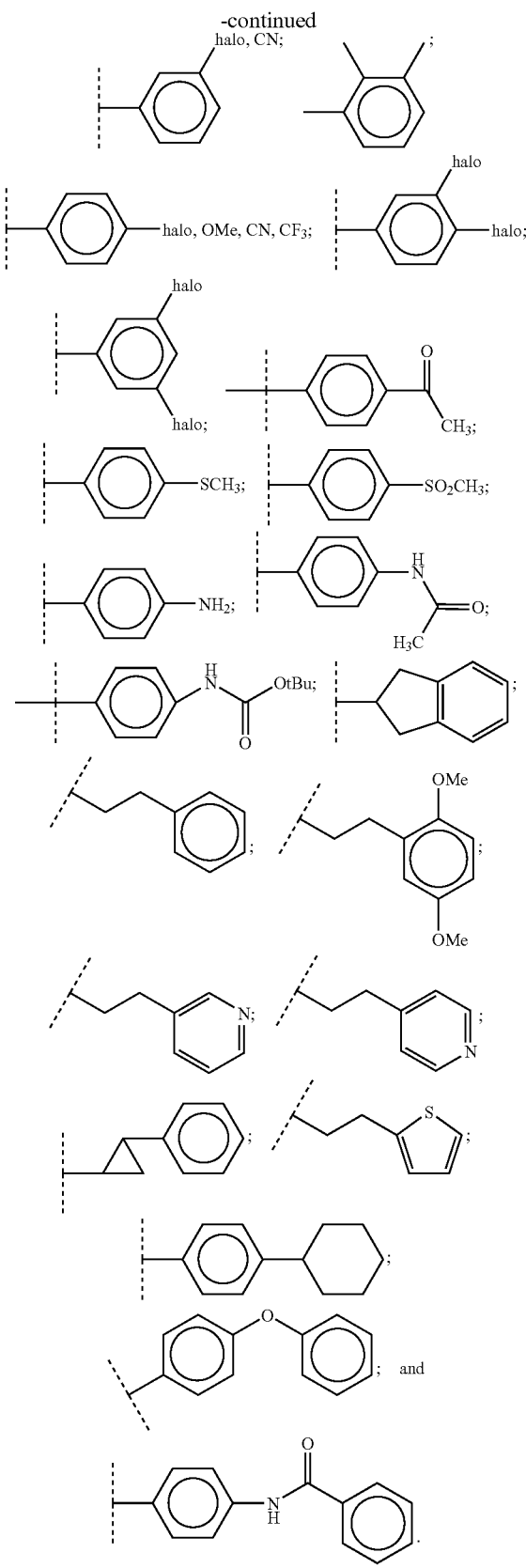

23. A compound according to claim 1, wherein $R^3$ is selected from the group consisting of:

24. A compound selected from the compounds of the following formula:

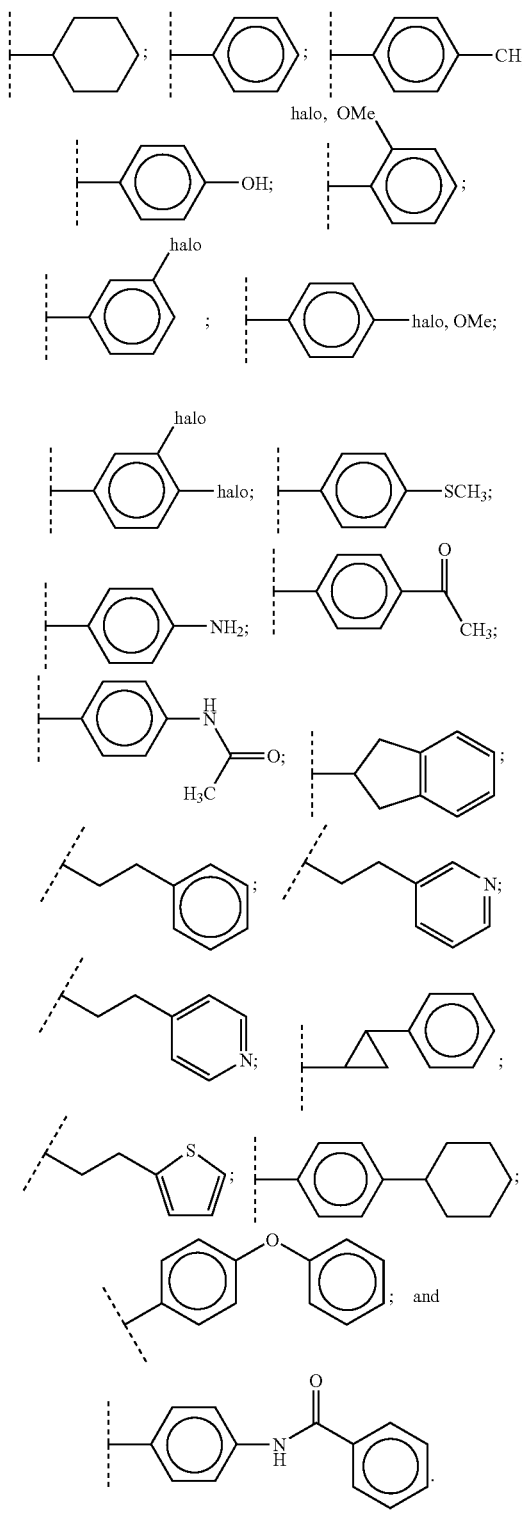

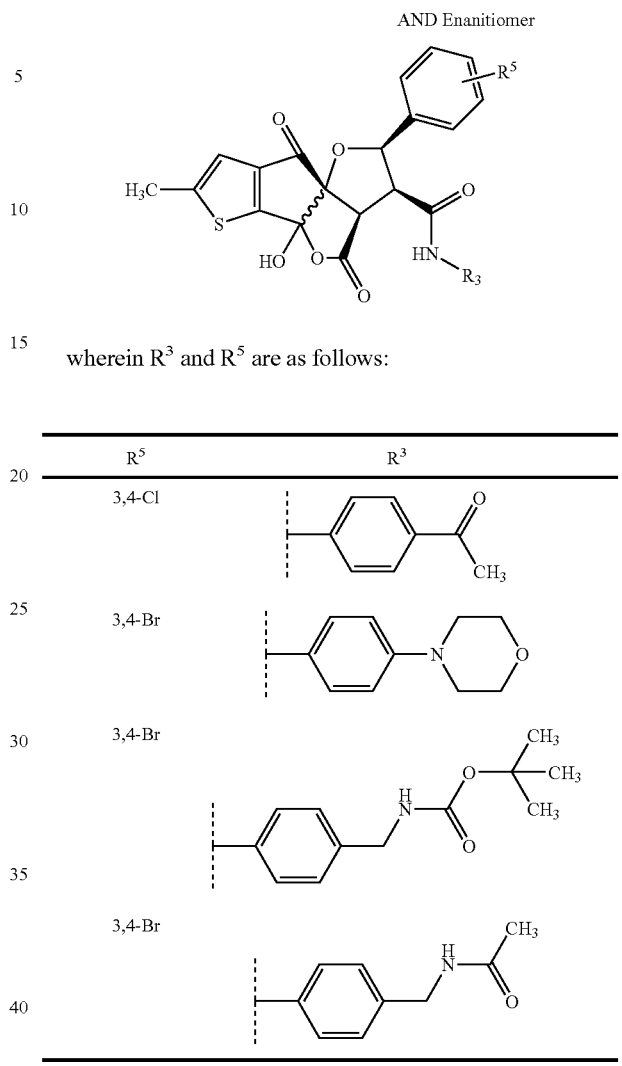

wherein $R^3$ and $R^5$ are as follows:

| $R^5$ | $R^3$ |
|---|---|
| 3,4-Cl | 4-acetylphenyl |
| 3,4-Br | 4-morpholinophenyl |
| 3,4-Br | 4-(Boc-aminomethyl)phenyl |
| 3,4-Br | 4-(acetamidomethyl)phenyl |

25. A pharmaceutical composition comprising an anti-papillomavirus virally effective amount of a compound of formula (I") or (I'"), according to claim 1, or a therapeutically acceptable salt or ester thereof, in admixture with a pharmaceutically acceptable carrier medium or auxiliary agent.

26. A method for treating a papillomavirus viral infection in a mammal by administering to the mammal an anti-papilloma virus virally effective amount of the compound of claim 1 or a therapeutically acceptable salt or ester thereof.

27. A method for inhibiting the replication of papillomavirus by exposing the virus to an effective amount of a compound of claim 1 or a therapeutically acceptable salt or ester thereof.

28. A method of preventing perinatal transmission of HPV from mother to baby by administering a compound of claim 1 or a therapeutically acceptable salt or ester thereof to the mother prior to giving birth.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Primer sequence

<400> SEQUENCE: 1
gcccctaact ccgcccatcc cgc                23

<210> SEQ ID NO 2
<211> LENGTH: 23
<212> TYPE: DNA
<213> ORGANISM: Artificial Sequence
<220> FEATURE:
<223> OTHER INFORMATION: Primer sequence

<400> SEQUENCE: 2
accagaccgc cacggcttac ggc                23